United States Patent
Ziaie et al.

(10) Patent No.: US 9,737,244 B2
(45) Date of Patent: Aug. 22, 2017

(54) SENSOR HAVING FERROGEL WITH MAGNETIC PARTICLES

(71) Applicants: Purdue Research Foundation, West Lafayette, IN (US); Regents of the University of Minnesota, Minneapolis, MN (US)

(72) Inventors: Babak Ziaie, West Lafayette, IN (US); Ronald A. Siegel, Minneapolis, MN (US)

(73) Assignees: Purdue Research Foundation, West Lafayette, IN (US); Regents of the University of Minnesota, Minneapolis, MN (US)

( * ) Notice: Subject to any disclaimer, the term of this patent is extended or adjusted under 35 U.S.C. 154(b) by 615 days.

(21) Appl. No.: 13/800,860

(22) Filed: Mar. 13, 2013

(65) Prior Publication Data

US 2013/0245402 A1    Sep. 19, 2013

Related U.S. Application Data

(60) Provisional application No. 61/609,960, filed on Mar. 13, 2012.

(51) Int. Cl.
*A61B 5/1455* (2006.01)
*A61B 5/145* (2006.01)
(Continued)

(52) U.S. Cl.
CPC ...... *A61B 5/14503* (2013.01); *A61B 5/14532* (2013.01); *G01N 27/72* (2013.01); *A61B 5/05* (2013.01)

(58) Field of Classification Search
None
See application file for complete search history.

(56) References Cited

U.S. PATENT DOCUMENTS 6,201,980 B1    3/2001  Darrow et al.
6,310,387 B1   10/2001  Seefeldt et al.
(Continued)

OTHER PUBLICATIONS

Alexeev, V.L., "High Ioinic Strength Glucose-sesing Photonic Crystal," American Chemical Society Copyright 2003, 10.1021/ac/030021m CCC: $25.00, Analytical Chemistry, vol. 75, No. 10, May 15, 2003 (8 pgs.).

(Continued)

*Primary Examiner* — Eric Winakur
*Assistant Examiner* — Marjan Fardanesh
(74) *Attorney, Agent, or Firm* — Lee & Hayes, PLLC; Christopher J. White

(57) ABSTRACT

A sensor for detecting a condition includes a hydrogel configured to change thickness or volume in response to the condition. Magnetic particles are arranged in the hydrogel so that a magnetic property of the hydrogel changes with changes of thickness or volume of the hydrogel. Some such sensors include a magnetic-field detector that measures the magnetic field of the hydrogel. Other such sensors include a device coil is arranged with respect to the hydrogel so that changes in the magnetic property modulate an electrical property of the sensor. A sensing system using such a sensor includes a reader spaced apart from the sensor and including a reader coil and a resonance detector coupled to the reader coil to detect a the resonant frequency of the sensor. Changes in the magnetic property detectably modulate the resonant frequency.

15 Claims, 25 Drawing Sheets

(51) Int. Cl.
*G01N 27/72* (2006.01)
*A61B 5/05* (2006.01)

(56) References Cited

U.S. PATENT DOCUMENTS

| | | | |
|---|---|---|---|
| 6,480,730 B2 | 11/2002 | Darrow et al. | |
| 6,750,311 B1 | 6/2004 | Van Antwerp | |
| 6,972,658 B1 | 12/2005 | Findley et al. | |
| 2002/0032380 A1* | 3/2002 | Acker | A61B 8/4254 600/439 |
| 2002/0115740 A1* | 8/2002 | Beuhler | C08F 8/00 522/152 |
| 2006/0264715 A1* | 11/2006 | Mir | A61B 5/1411 600/309 |
| 2011/0312004 A1 | 12/2011 | Chinnayelka et al. | |

OTHER PUBLICATIONS

Asher, Sanford A. et al., "Photonic Crystal Aqueous Metal Cation Sensing Materials," American Chemical Society, Copyright 2003, 10.1021/ac/026328n CCC: $25, Analytical Chemistry, vol. 75, No. 7, Apr. 1, 2003 (8pgs.).

Bashir, R et al., "Micromechanical Cantilever as an Ultrasensitive pH Microsensor," Citation: Appl. Phys. Lett. 81, 3091 (2002): doi: 10.1063/1.1514825 (4 pgs.).

Liu, Robin H. et al., "Fabrication and Characterization of Hydrogel-Based Microvalves," 1057-7157/02$17.00, Copyright 2002, IEEE, Journal of Microelectromechanical Systems. vol. 11, No. 1, Feb. 2002 (9 pgs.).

Gawel, Kamila et al., "Logic Swelling Response of DNA-Polymer Hybrid Hydrogel," Soft Matter, 2011, 7, 4615-4618, View Article Online/Journal Homepage/Table of Contents for this Issue: www.rsc.org/softmatter, (4 pgs.).

Gerlach, Gerald et al., "Chemical and pH Sensors Based on teh Swelling Behavior of Hydrogels," 0925-4005/$ see front matter, copyright 2005, Elsevier B.V, doi: 10.1016/j.snb.2005.03.040 (7 pgs.).

Herber, S. et al, A Miniaturized Carbon Dioxide Gas Sensor Based o n Sensing of pH-Sensitive Hydrogel Swelling with a Pressure Sensor, Biomedical Microdevices 7:3, 197-204, 2005, copyright 2005 Springer Science + Business Media, Inc. Manufactured in The Netherlands (8 pgs.).

Satarkar, Nitin S. et al., "Magnetic Hydrogel Nanocomposites for Remote Controlled Pulsatile Drug Release," Journal of Controlled Release 130 (2008) 246-251, 0168-3659/$ see front matter, copyright 2008 Elsevier B.V., doi: 10.1016/j.conrel.2008.06.008 (6 pgs.).

Baldi, Antonio et al., "A Microstructured Silicon Membrane with Entrapped Hydrogels for Environmentally Sensitive Fluid Gating," 0925=-4005/$—see front matter, copyright 2005 Elsevier B.V., doi: 10.1016/j.snb.2005.04.020, Sensors and Actuators B 114 (2006) 9-18 (9 pgs.).

Lei, Ming et al., "Hydrogel-based Microsensors for Wireless Chemical Monitoring," Birck Nanotechnology Center, Purdue University Purdue e-Pubs, Paper 353. http://dos.lib.purdue.edu/nanopub/353 (11 pgs.).

Lei, Ming et al., "A Hydrogel-based Implantable Micromachined Transponder for Wireless Glucose Measurement," Military Metabolic Monitoring, Diabetes Technology & Therapeutics, vol. 8, No. 1, 2006, copyright Mary Ann Liebert, Inc. (11 pgs.).

Baldi, Antonio et al., "A Hydrogel-Actuated Environmentally Sensitive Microvalve for Active Flow Control," Journal of Microelectromechical Systems, vol. 12, No. 5, Oct. 2003, 1057-7157/03$17.00, copyright 2003 IEE (9 pgs.).

Orthner, M. P. et al., "Development, Fabrication, and Characterization of Hydrogel Based Piezoresistive Pressure Sensors with Perforated Diaphragms," 0924-4247/$—see front matter, Copyright 2010, Elsevier, B.V., doi: 10.1016/j.sna.2010.05.023 (10 pgs.).

Miyata, Takashi et al., "A Reversibly Antigen-Responsive Hydrogel," 1999 Macmillan Magazines Ltd., Nature/vol. 399, Jun. 24, 1999, www.nature.com pp. 766-769 (4 pgs.).

Zhao, Xuanhe et al., "Active Scaffolds for On-Demand Drug and Cell Delivery," www.pnas.org/cgi/doi/10.1073/pnas.1007862108 (6 pgs.).

Tierney, Sven et al., "Determination of Glucose Levels Using a Functionalized Hydrogel—Optical Fiber Biosensor: Toward Continuous Monitoring of Blood Glucose in Vivo," 10.1021/ac900019k CCC: $40.75 Copyright 2009 American Chemical Society, Analytical Chemistry, vol. 81, No. 9, May 1, 2009, (7 pgs.).

Zu, Zhi et al., "An Aptamer Cross-Linked Hydrogel as a Coloimetric Platform for Visual Detection," Angewandte Chemie, Angew. Chem. Int. Ed. 2010, 49, Wiley Interscience/DOI: 10.1002/anie.200905570, pp. 1052-1056 (5 pgs.).

Lin, Genyao, "Development of Glucose and pH Sensitive Hydrogels for Microfabricated Biomedical Sensor Arrays," The Smithsonian/NASA Astrophysics Data System, found at http://adsabs.harvard.edu/abs/2010PhDT . . . 33L (2 pgs.).

Gawel, Kamila et al., "Logic Swelling Response of DNA-Polymer Hybrid Hydrogel," University of Minnesota—Twin Cities, published on Apr. 11, 2011 on http://pubs.rsc.org doi: 10.1039/C1SM05221G, Soft Matter, 2011, 7, 4615-4618 (4 pgs.).

* cited by examiner

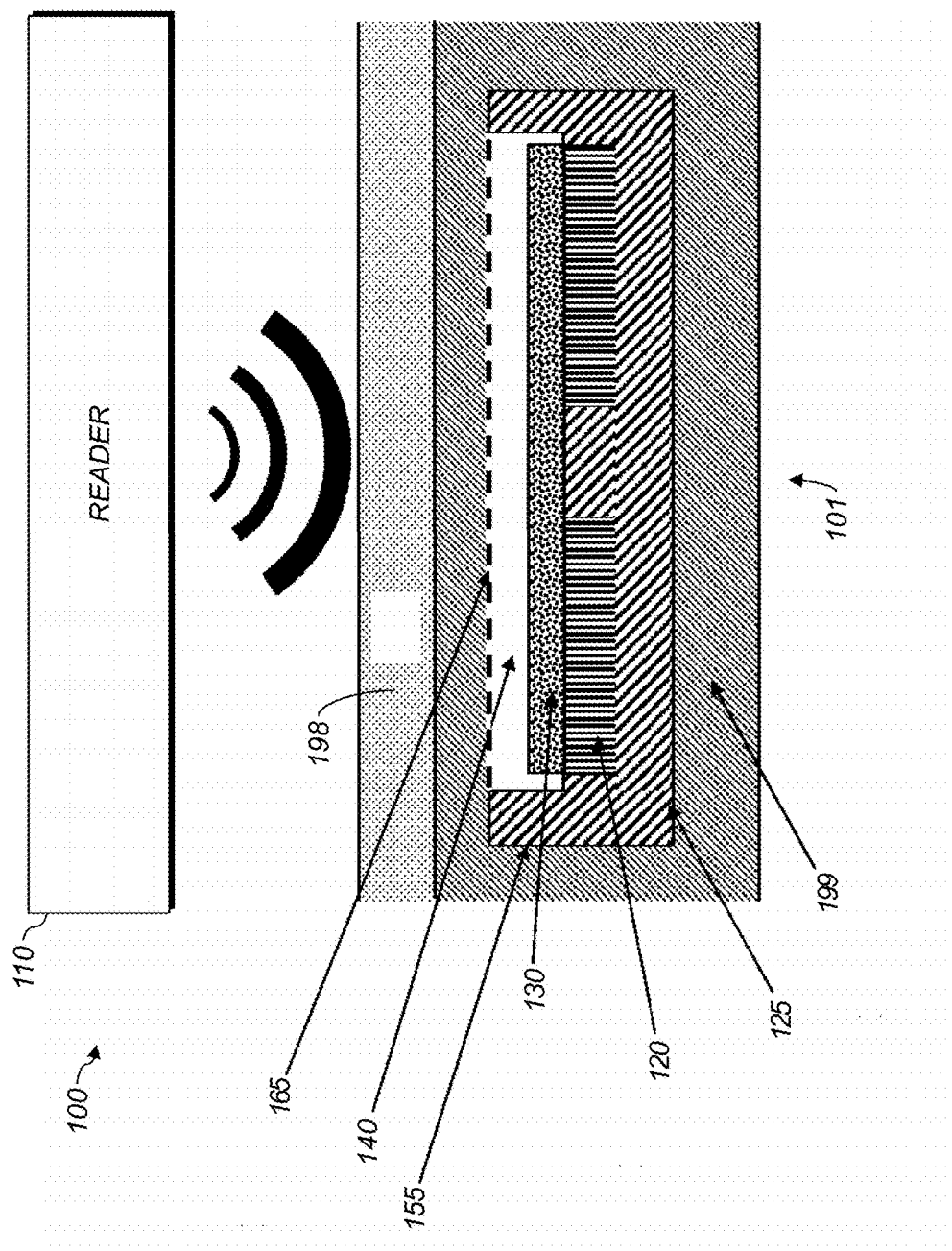

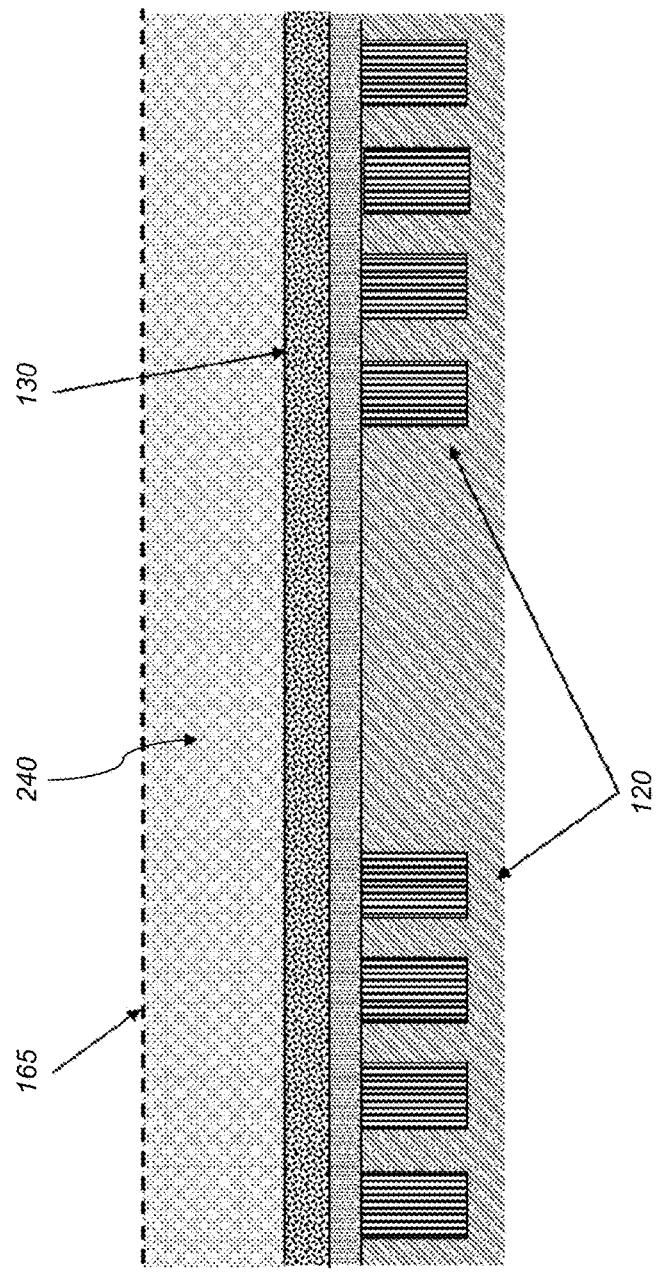

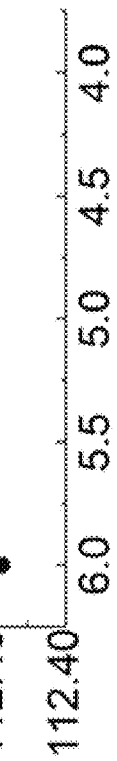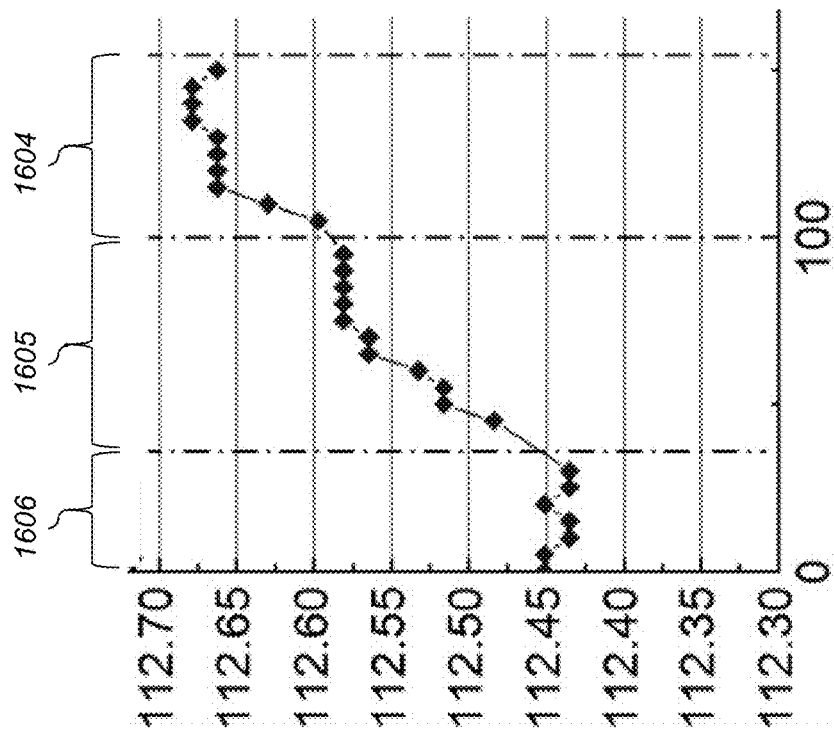
FIG. 16B
FIG. 16A

SENSOR HAVING FERROGEL WITH MAGNETIC PARTICLES

STATEMENT OF FEDERALLY SPONSORED RESEARCH OR DEVELOPMENT

This invention was made with government support under Contract No. ECCS-1128169 awarded by the National Science Foundation. The government has certain rights in the invention.

CROSS-REFERENCE TO RELATED APPLICATION

This application is a nonprovisional application of U.S. Provisional Application Ser. No. 61/609,960, filed Mar. 13, 2012, and entitled "Sensor Having Ferrogel Responsive to Changes in Chemical Environment in the Presence of a Magnetic Field," the entirety of which is incorporated herein by reference.

TECHNICAL FIELD

The present disclosure generally relates to sensors, and in particular to a class of sensors responsive to changes in chemical, physical, or biological environment.

BACKGROUND

Environmentally sensitive hydrogels have been to focus of extensive investigation over the past several decades. These crosslinked polymeric systems can be engineered to swell and shrink (de-swell) in response to a variety of physical, chemical, and biological stimuli. Hydrogels therefore can operate as transducers without the requirement for an on board power source. Much research and development in this area has been towards actuating systems in which a drug embedded hydrogel can be directed to swell and release its payload in response to pH, temperature, magnetic field and other stimuli. Recently, environmentally sensitive hydrogels have been integrated with micromachined and MEMS structures in order to expand their capabilities by coupling them to hard inorganic materials. An example is described by Lei et al. in "A Hydrogel Based Implantable Micromachined Transponder for Wireless Glucose Measurement," Diabet. Technol. Therap. 2006; 8:112-22. A glucose-sensitive hydrogel was coupled to the plate of a micromachined capacitive sensor. Specifically, swelling of the glucose-sensitive hydrogel deflected the moving plate of a MEMS capacitor. The resonant frequency of a parallel LC circuit in which the capacitor was the sensing element thus changed with glucose concentration, permitting remote glucose measurement by monitoring that resonant frequency Such devices, however, require complicated fabrication processes, e.g., snug-filling of a small cavity with hydrogel. Some such sensors require being hermetically sealed against aqueous environments but still providing an electrical feedthrough. Sensors have also been developed that measure the pressure exerted by a hydrogel when it swells. Sensors have also been developed that measure temperature, pH and salt concentration, by combining a suitably sensitive hydrogel with a MEMS capacitor. Actuators have been developed that stimulate a hydrogel electromagnetically. Temperature changes generated inside the hydrogels by the electromagnetic fields, which can, e.g., heat superparamagnetic nanoparticles embedded in the hydrogel, causes swelling and shrinking of the hydrogels.

The past several decades have witnessed marked improvements in the understanding and treatment of diabetes mellitus, a disorder which affects millions in the U.S. and abroad, with increasing incidence nationally and internationally due to lifestyle changes. While acute mortality due to diabetes can be averted by regular paraprandial injections of insulin, long term morbidities due to chronic hyperglycemia (condition caused by high glucose levels) remain a challenge.

Diabetes refers to disorders in glucose homeostasis and hence energy storage and use by the body. There are two major types of diabetes. In Type I or juvenile onset diabetes, pancreatic beta cells, which normally would secrete insulin, a regulator of blood glucose level, are destroyed. Persons with Type I diabetes exhibit wide swings in blood glucose, including episodes of hyperglycemia (blood glucose too high) following meals. Over a life time, hyperglycemia can lead to degeneration of nerve, muscle, and connective tissue, with shortened life span and degraded quality of life. Blindness or loss of extremities can occur in extreme cases. Type I diabetes can be controlled by judicious injection of insulin, either through a syringe or a catheter connected to a wearable pump. Care must be taken, however, that insulin administration does not drive blood sugar level too low (hyperglycemia), as this may lead to disorientation, coma, or death. The Type I diabetic must therefore monitor his or her glucose level frequently to administer the correct amount insulin at the appropriate time.

In Type II or adult onset diabetes, insulin is not utilized properly to regulate blood glucose level. Type II diabetics cannot be treated by insulin alone, and a number of drugs have been developed to improve glucose homeostasis. Incidence of Type II diabetes has sharply increased both in the US and internationally, primarily due to consumption of unhealthy foods and sedentary lifestyle. Diet and exercise are important regulators of glucose metabolism in treating Type II diabetes, and glucose monitoring may play an increasing role by providing "on-line" feedback to the patient and caregiver regarding these behavioral aspects.

A secondary physiological consequence of diabetes is reduced control of blood pH, and diabetics exhibit so-called "acidotic" and "alkalotic" swings. Since blood pH is normally constant at pH 7.4, these swings, besides being detrimental, reveal the state of health of the diabetic. Thus, a continuous monitor of blood pH, in tandem with blood glucose level, may provide useful complementary information for evaluating treatment.

Largely due to the landmark Diabetes Control and Complications Trial (DCCT), it is widely believed that improved health and quality of life for diabetics is correlated with maintenance of blood glucose levels within relatively tight bounds. DCCT established that minimizing hyperglycemia helps forestall development of long term morbidities, which are attributed to long term hyperexposure of tissues to glucose. However, a tendency among some patients to "overinsulinize" themselves in response to hyperglycemic episodes can lead to dangerous hyperglycemic and hypoglycemic swings.

Typically, patients monitor their blood glucose intermittently using a finger stick method. However, finger sticks are uncomfortable and provide time-separated, discrete observations of blood glucose level, which changes continuously as a function of time. Indeed, based on the current method of intermittent monitoring of glucose, some of the fluctuations, including sudden hypoglycemic episodes, can be missed.

Transcutaneous glucose electrodes generally pose challenges such as infection due to the transcutaneous nature of the sensors, enzyme denaturation in enzyme based sensors, degradation, and poisoning. Electrodes that rely on the enzymatic (glucose oxidase) oxidation of glucose and subsequent conversion to electric current, are presently used in commercial sensors, including CGMS Gold™ (Medtronic Minimed™), Seven™(DexCom™), and Navigator™ (Abbott™/Therasense™), with FDA approval limited to one week use. While some of these challenges can be addressed by incorporating catalase, and while such electrodes represent a step forward in diabetes management, practical challenges remain, including the need for frequent (often daily) calibration against blood glucose obtained by finger-prick procedures.

Continuous Glucose Monitors (CGMs) can provide better management of glucose level. It is important for diabetic patient to identify fluctuations and trends in their glucose levels. This reduces the probability of emergency situations (e.g., hypoglycemic episodes, indicated by shaking, sweating, fast heartbeat, and impaired vision), particularly if monitoring is performed autonomously. However, current continuous glucose monitors have a number of disadvantages. They puncture the skin, need to be periodically replaced (as often as every week) and calibrated (as often as every 12 hours), restrict motion, are not waterproof (some can tolerate water but few or none can survive hot water), and are expensive.

Recently, an implantable glucose oxidase/catalase-based sensor was shown to reliably monitor glucose fluctuations in diabetic pigs for more than one year. In this disk-shaped system (diameter 3.4 cm, thickness 1.5 cm), the enzyme electrode was packaged with a battery and microelectronics for radiotelemetry. The sensor, implanted into tissue, exhibited short, 6-10 min "dynamic delays", i.e. latencies in tracking up- and downswings in blood glucose concentration. Delays were attributed primarily to mass transfer in tissue. Also important was the demonstration of stable tissue encapsulation, with adequate capillary supply.

Glucose can be "sampled" by reverse iontophoresis across the skin and analyzed electrochemically. Glucowatch™, a product based on this concept, received FDA approval, but was withdrawn from the market due to skips in intermittent (20 min duty cycle) measurements and the need for daily calibration. Ultrasound followed by vacuum extraction across the skin and electrochemical detection, has also been proposed.

Blood glucose sensing by absorption and reflectance of near- and far-IR radiation, or by surface-enhanced Raman scattering (SERS), is under investigation. These optical techniques, while attractive since electromagnetic (EM) energy can be generated and sensed noninvasively, exhibit difficulties in establishing unambiguous correlation between signal and true blood glucose level due to interfering analytes and scattering by intervening tissues. They also require sophisticated, bulky, and expensive readout instrumentation.

In addition to glucose monitoring, detecting environmental changes, specifically chemical changes, has also received significant attention over the past few decades. Some of the sensors for detecting chemical changes are part of complex industrial systems.

There is, therefore, a continuing need for a simple system that allows detection of chemical environmental changes, and that overcomes challenges accompanied with present systems including the transcutaneous glucose electrodes and other systems described above. Continuous or substantially continuous monitoring can provide data that can be recorded, stored, locally analyzed, communicated over a network, studied for trends over time, and be used in a system with a feedback path to provide corrective actions when needed.

Continuous sensing, in conjunction with predictive algorithms, can improve guidance of these corrective actions to minimize episodes associated with conditions outside of normal ranges. The advantage of continuous monitoring may extend to Type II diabetes. Here, continuous monitoring of glucose concentration in the body can help physicians and patients evaluate pharmacologic and/or behavioral therapies.

SUMMARY

According to an aspect of the invention, there is provided a sensor for detecting a condition, the sensor comprising:
  a) a hydrogel configured to change thickness or volume in response to the condition;
  b) a plurality of magnetic particles arranged in the hydrogel so that a magnetic property of the hydrogel changes with changes of thickness or volume of the hydrogel; and
  c) a device coil arranged with respect to the hydrogel so that changes in the magnetic property modulate an electrical property of the sensor.

According to various aspects, there is provided a sensor for detecting a condition, the sensor comprising:
  a) a hydrogel configured to change thickness or volume in response to the condition;
  b) a plurality of magnetic particles arranged in the hydrogel so that a magnetic field of the hydrogel changes with changes of thickness or volume of the hydrogel; and
  c) a magnetic-field detectoroperatively arranged to measure the magnetic field of the hydrogel.

According to another aspect of the invention, there is provided a sensing system for detecting a condition, the system comprising:
  a) a sensor having:
    i) a hydrogel configured to change thickness or volume in response to the condition;
    ii) a plurality of magnetic particles arranged in the hydrogel so that a magnetic property of the hydrogel changes with changes of thickness or volume of the hydrogel; and
    iii) a device coil arranged with respect to the hydrogel so that changes in the magnetic property modulate a resonant frequency of the sensor; and
  b) a reader spaced apart from the sensor, the reader including:
    i) a reader coil;
    ii) a resonance detector coupled to the reader coil and adapted to detect the resonant frequency of the sensor; and
    iii) a power source adapted to supply RF energy to the external coil.

Various aspects advantageously provide sensors that can operate wirelessly, i.e., without a mechanical connection to a reader or other device. Various aspects do not require an external power source. Sensors can be designed according to various aspects to sense a variety of conditions.

Various aspects provide an implantable wireless glucose sensor. This is a small wireless sensor implanted under the skin with an external system to readout results. This can advantageously significantly reduce the risk of infection due to skin puncture. In an example, a wireless reader is incorporated in a watch and a ferrogel sensor is implanted into the user's arm under the wrist. Wearing the watch therefore is all that is required to perform continuous glucose monitoring.

Compared to existing CGM sensors (~25 mm×~50 mm), various aspects are as small as 2 mm×2 mm×200 µm, and are suitable for implantation. Various aspects have long working lifetimes and so do not need to be replaced weekly. Once implanted, the sensor does not move, unlike some prior sensors in which movement of the sensor due to body motion compromises the integrity of the measurements.

In various aspects, a wireless transponder for measurement of glucose in biological milieus includes a planar inductor or coil fabricated on a substrate. A glucose sensitive ferrogel (hydrogel plus magnetic micro- or nano-particles) is immobilized and patterned on top of the inductor. The inductor and ferrogel are packaged inside a hard-shell container and separated from body fluids by a nanoporous membrane. In various aspects, the swelling and shrinking of the ferrogel result in a change in inductance which can be measured from outside the body using an interrogator ("reader"). In various aspects, the inductor (coil) is patterned on a polymer, metallic, or ceramic substrate. In various aspects, the container includes polymer, metal, or ceramic. In various aspects, the ferrogel is patterned in various shapes using micro-fabrication methods in order to improve its performance.

BRIEF DESCRIPTION OF DRAWINGS

FIG. 1A is a schematic of a system illustrating an external electronic reader (transmitter/receiver) and an implantable device, according to various aspects.

FIG. 2B is a cross-sectional schematic view of the implantable device of FIG. 1A, depicted in a second state responsive to a second concentration of the chemical environment.

FIG. 16A shows a time series of measured resonant frequency.

FIG. 16B shows the measured resonance frequency of the ferrogel sensor in response to step changes in pH.

DETAILED DESCRIPTION

Figure 1B:
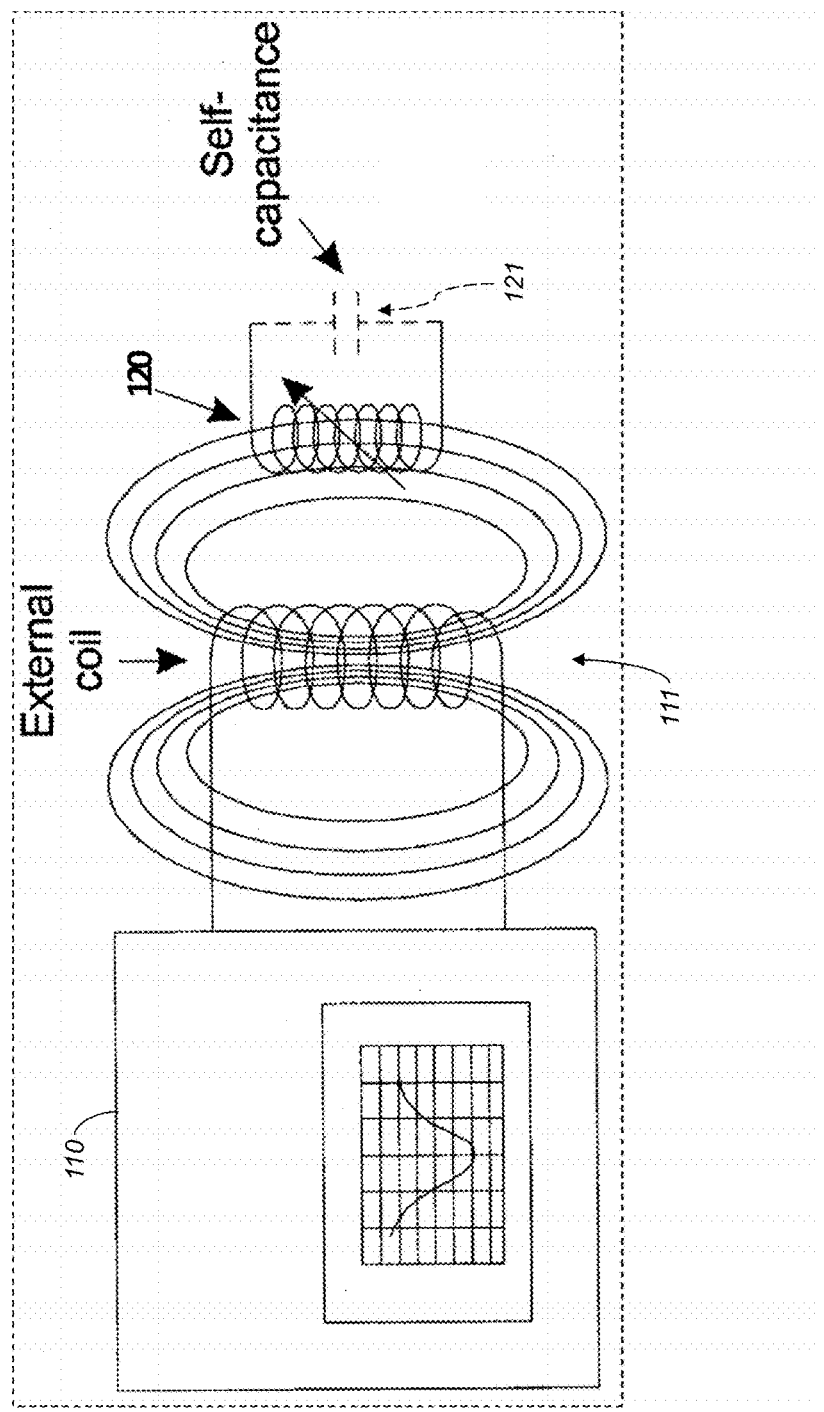
FIG. 1B is an electrical-magnetic schematic of the system of FIG. 1A.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A system having an environmental sensor is disclosed. The system includes a sensor assembly including a base, a fluid-swollen crosslinked polymer gel member including magnetic particles (also referred to as ferrohydrogel, ferrogel, and hydrogel) positioned over the base, a membrane coupled to the base and positioned over the ferrohydrogel member. Some sensors described herein include an embedded conductive coil or "device coil" positioned adjacent the ferrohydrogel member. The membrane is configured to allow passage of fluid across the membrane and into contact with the ferrohydrogel member and to block particles of a predetermined size or electrical charge, e.g., proteins and cells, suspended in the fluid. The ferrohydrogel member is configured to swell and shrink when the ferrohydrogel is in contact with the fluid, responsive to physical or chemical changes in the fluid. Swelling and deswelling alters the magnetic permeability of the hydrogel, or other magnetic properties thereof, by changing the density of the magnetic particles therein. This change in permeability can be remotely detected in various ways. In various embodiments, the hydrogel's magnetic permeability is detected using the Hall effect. In other embodiments, the hydrogel's magnetic-permeability change is detected using a superconducting quantum interference detector (SQUID). In other embodiments, the ferrogel is configured to modulate inductance and self-resonant frequency of a combination of the device coil and the ferrogel as the gel swells and shrinks. In some such embodiments the system further includes an external coil configured to excite the device coil. Systems according to various aspects are configured to detect changes in at least one of temperature, glucose, pH, concentration of urea, sugars, metal ions, concentration of salts, or concentrations of other chemicals.

A physical or chemical monitoring system is disclosed. The system includes an external electronic reader (transmitter/receiver) and a sensor. The sensor includes a ferrohydrogel configured to change one of thickness and volume, or both, in response to changes in physical variables such as temperature, or in concentrations of chemicals in the sensor's environment. The external reader is configured to communicate with an electronic reader to determine inductance and capacitance of the sensor.

A sensor that can provide continuous readout of temperature or chemical concentration is disclosed herein. A wireless chemical environment monitoring system to continuously monitor chemical levels in a subcutaneous space is disclosed herein. Various sensors herein include a hydrogel.

Generally a hydrogel is a water swollen polymer network containing chemical groups that are sensitive to an environmental stimulus. When the stimulus is physical, e.g., a change in temperature, the polymer's interaction with water changes such that the hydrogel swells or shrinks. Swelling and shrinking can also result from a chemical interaction between an analyte of interest and a moiety that is incorporated within the polymer network. In either case, volume change can be regarded as a signal transduction, or in some cases, as an amplification.

As used herein, the term "condition" refers generally to something that can be measured or transduced with a hydrogel. Examples of conditions include physical properties such as temperature or pH and presence or absence of an analyte, either chemical or biochemical. Conditions can be discrete-valued (is glucose present or not?) or analog (what is the pH?).

Since hydrogels typically are highly hydrated, they provide an essentially aqueous environment allowing ready access of analyte to the sensing moiety. In various aspects a particular type of hydrogel, which includes co-immobilized molecules and/or nano-objects designed to assist in reporting the presence of the analyte, is used. Changes in the characteristics of the hydrogel due to stimuli, e.g., changes in thermal or chemical environment, can be detected by monitoring the hydrogel. Application of a magnetic field to a sensor including the hydrogel can be used to ascertain changes in the hydrogel.

The devices and systems disclosed herein can be used to provide a wireless and battery-less biomedical sensor and accompanying system that can monitor physiological variables such as pH and glucose concentration. These targets are relevant to diabetes. Various aspects can be used for pH or glucose sensing and monitoring. Other aspects of systems and sensors herein are general platforms for detection of other analytes, physiological or otherwise, and other chemical or thermal environments.

The sensor can be microfabricated to have area less than about 1 cm$^2$ and a thickness less than about 1 mm. The sensor can be implanted, e.g., in an outpatient clinic, and following healing it can be configured to function for months or years without a need for replacement.

FIG. 1A shows a schematic for a system according to various aspects. Various aspects operate with electromagnetic fields in the radio-frequency (RF) range. The system 100 includes an external electronic reader 110 and a microsensor 101 including a microresonator circuit (including coil 120 and hydrogel 130, discussed below). The external electronic reader 110 can be a receiver or a transmitter/receiver (transceiver). In addition, the external reader 110 can be coupled to the microsensor 101 via a wire, or utilize a wireless configuration.

The microresonator circuit includes device coil(s) 120 embedded in a substrate 125, covered by a chemical environmentally sensitive, swellable ferrohydrogel 130. The hydrogel 130 is of a type that includes paramagnetic or superparamagnetic nanoparticles ("SPNs"). This circuit has a substantially constant capacitance, C. The capacitance is a function of coil 120 geometry and properties of the substrate 125. The device coil's inductance, L, depends on coil(s) 120 geometry (e.g. number of turns). The inductance also depends on the swelling of the hydrogel 130, since the ferrite nanoparticle density and ferrogel thickness governs the magnetic permeability. Hence, the resonant frequency depends on temperature and/or concentration of a chemical. In Eq. (1), $$f_{res} = \frac{1}{2\pi\sqrt{LC}} \quad (1)$$

$f_{res}$ is the resonant frequency, L is the inductance, and C is the capacitance. L, C, and $f_{res}$ are examples of electrical properties of the microsensor 101.

Resonant frequency can be detected by detecting a dip in impedance to radio frequency (RF) energy provided by an external coil 111 coupled to a frequency analyzer in reader 110 (FIG. 1b), or by using a phase lock-in circuit connected to the external coil 111 to lock in to the resonant frequency. It should be appreciated that the external electronic reader 110 depicted in FIG. 1A represents either of these approaches, which are referred to generically as "resonance detectors." The implantable device 101 according to various aspects requires no internal power source, battery, or internal data processing circuit. As a result, packaging of the implantable device is simplified.

Figure 12:
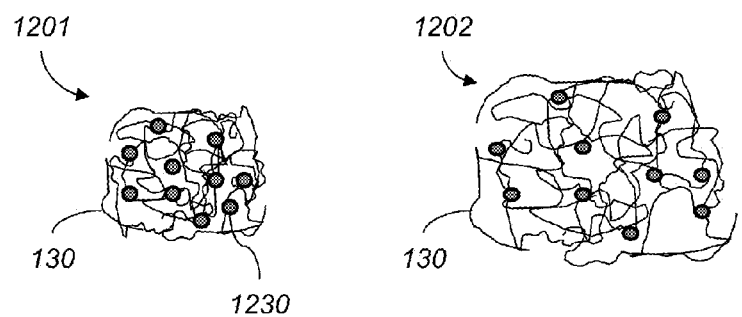
FIG. 12 shows an example of internal structure of a ferrogel.

FIG. 12 shows an example of internal structure of a ferrogel. The ferrogel 130 is prepared by randomly dispersing superparamagnetic ferroparticle-embedded polystyrene beads throughout the network before polymerization. The ferroparticles are thus physically trapped in the polymer network. Poly (methacrylic acid-co-acrylamide) (MAA-co-AAm) pH-sensitive hydrogels can be used. In this example, an increase in pH drives the ferrogel towards state 1202, and a decrease in pH drives the ferrogel towards state 1201.

In various aspects, the inductance of the sensor (e.g., microsensor 101, FIG. 1A) is altered by two competing mechanisms. As the ferrogel expands, the density of SPNs 1230 reduces, while the length of magnetic flux lines passing through the ferrogel sheet increases. Overall, the effect of longer magnetic flux pathway coupled with the SPNs prevails over lower SPN density, and the inductance of the sensor increases as the ferrogel swells. This increased inductance results in a lower resonant frequency of the sensor.

In FIG. 1A, a cross sectional view of the inductor (coil 12) is depicted. The inductor is a planar device coil, best depicted in FIG. 2D as described below, with terminals positioned outside and inside the device coil. The device coil can be an inductor in a microchip or an inductor printed on a plastic substrate.

The concept of energizing the microresonator circuit which includes a coil or coils 120 (L) and a capacitance 121

(C) is demonstrated in FIG. 1B. Radio frequency (RF) energy supplied by a power source (e.g., as discussed below with reference to FIG. 1C) in the electronic reader via the external coil, as shown, excites the microresonator circuit. As depicted in FIG. 1B, the external coil can be configured to broadcast a signal. The signal is picked up by the device coil(s) of the implantable device. The impedance of the implantable device, partially defined by the L and the C, affects the broadcast signal and the effect is picked up by the impedance analyzer or the phase lock-in circuit described above (which would be part of the external electronic reader shown in FIG. 1A). The device coil(s) in the implantable device magnetically couples to the external coil and becomes part of the circuit which includes the external coil.

Figure 1C:
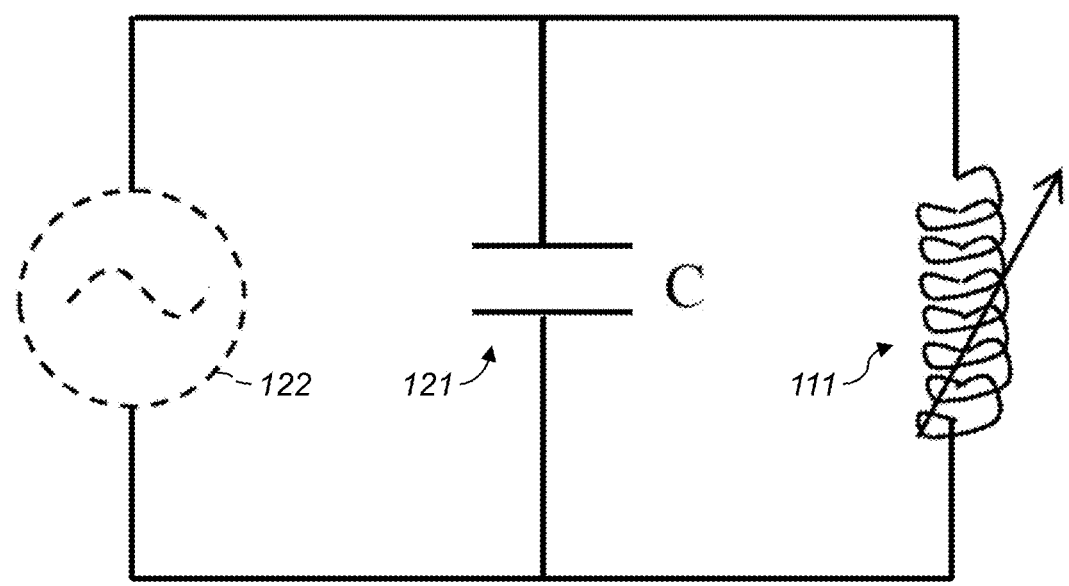
FIG. 1C is an electrical schematic showing a model of the implantable device depicted in FIG. 1A.

Referring to FIG. 1C an electrical model is presented. It should be noted that while there may be electrical resistance between various components, such resistance is not shown in FIG. 1C. The model includes a power source 122 that can be used to excite the passive elements of the implantable device. The source is shown in phantom since it is possible to have a system that does not include a source where a Hall-effect type sensor is used to sense movement of magnetic particles embedded in the hydrogel when the hydrogel swells and shrinks, as described further below. The capacitor 121 can be the parasitic capacitance of the structure depicted in FIG. 1A or an actual capacitor (not shown) coupled to the device coils. The variable inductance 111 includes device coils 120 and the hydrogel 130 with ferromagnetic particles embedded therein. On the one hand the ferromagnetic particles may be non-magnetized (i.e., the particles do not generate a magnetic field without being excited, thereby requiring the source shown in phantom) or magnetized (i.e., the particles generate a magnetic field without being excited, used with a Hall-effect type sensor or SQUID). Changes in glucose or other chemical environment can result in changes in the hydrogel 130 height which can result in changes in the inductance (i.e., lumped inductance resulting from the device coils 120 and the hydrogel 130 with embedded ferromagnetic particles), resulting in changes in natural (resonant) frequency of the implantable device. In summary, this is $\Delta\text{Glucose} \rightarrow \Delta h \rightarrow \Delta L \rightarrow \Delta f_{res}$. Thermally sensitive devices work in a similar manner, but with a temperature-sensitive hydrogel in place of the chemically-sensitive hydrogel.

The changes in the natural frequency can be detected using an electronic reader. Various schemes can be used to detect changes in the natural frequency of the implantable device. One method can be based on a phase dip measured at the input terminals of the external coil as a function of frequency occurring at the natural frequency of the implantable device. Another method can be based on a phase-lock scheme, where an external transceiver transmits a pulse near the natural frequency of the implantable device, and examines a reflected pulse from the implantable device. Measuring phase shift in the reflected signal can provide information about the natural frequency.

The implantable (subcutaneous or intraperitoneal) microsensor which can operate without internal batteries or data processing circuitry, as depicted in FIG. 1A, is now described. The device includes a PBA-based ferrohydrogel and does not involve enzymes or electrochemical reactions, so its mechanism of action is inert to surrounding tissues. Once implanted, chemical concentration dependent swelling of the ferrohydrogel can be interrogated continuously and wirelessly. The combination of small size and wireless operation provides advantages over sensors that are commercially available or are under research and development. Various aspects advantageously operate in the absence of enzyme-mediated bioelectrochemistry, permitting them to be used in a wider range of settings than other sensors. In various aspects, enzymes are incorporated into the device, providing a mechanism for chemical to mechanical transduction. Various aspects are inert to surrounding tissues and have long-term stability of sensitivity.

In the microsensor of FIG. 1A, inductance (L) varies due to swelling and shrinking of the chemical concentration sensitive ferrohydrogel, which alters magnetic permeability just above the device coil and distorts magnetic flux lines. The capacitance (C) is set by electrical polarizability (characterized by dielectric constant) between device coil turns, and between the device coil and the substrate. Device coil geometry, e.g. distance between turns will also affect capacitance. Capacitance can be substantially unaffected by the ferrohydrogel, and can be assumed constant provided fluid does not substantially invade the substrate and device coil volumes.

In the microsensor depicted in FIG. 1A, the hydrogel 130 is bonded on one end to the substrate, it is therefore configured to swell freely in the "vertical" direction, and not completely filling cavity 140, as depicted in the figure. Substantially none of the solid state elements of the sensor are deflected by hydrogel swelling, so considerations of mechanical strength are less important in the microsensor depicted in FIG. 1A. Also depicted is a ring 155 that is coupled to the substrate 125, e.g., continuously or by welding, which is used to support and hold a membrane 165. The microsensor is placed in the testing environment 199, e.g., under the skin 198 in contact with the intercellular fluid. The ring defines a fluid space 140 between the membrane 165 and the substrate 125. Within the fluid space, the hydrogel is free to swell and shrink when it comes in contact with chemical stimuli of varying concentrations.

Figure 2A:
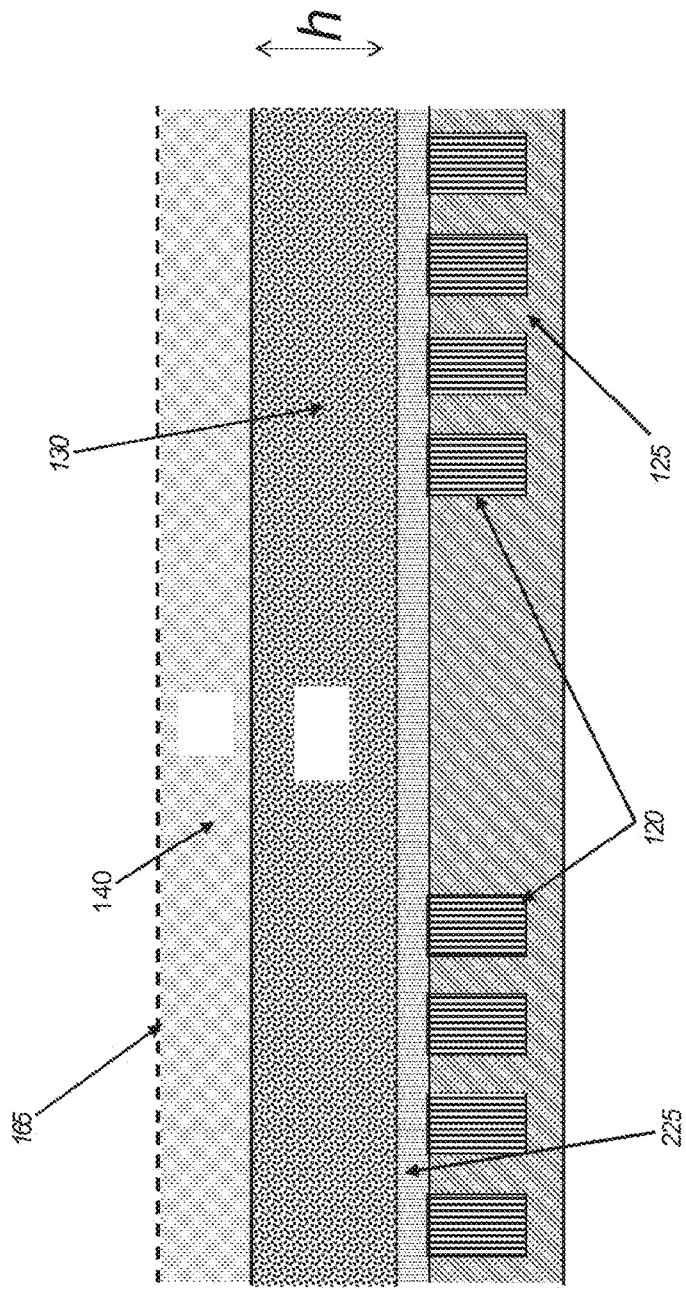
FIG. 2A is a cross-sectional schematic view of the implantable device of FIG. 1A, depicted in a first state responsive to a first concentration of a chemical environment.

FIG. 2A is a cross sectional schematic of the microsensor of FIG. 1A, further depicting the substrate 125, the device coil 120, and the hydrogel 130. The device coil 120 includes conductive material (e.g., metal) embedded in an insulating dielectric substrate 125, and is coated on top with a thin, waterproof insulating layer 225 (e.g., polyimide). The hydrogel 130 is bonded on top of the coating 225 and extends into a fluid space 140 (FIG. 1A) below the membrane 165. Because of bonding, changes in hydrogel swelling are manifested by a change in hydrogel thickness, h, from an initial "reference" thickness, $H_0$. The hydrogel contains immobilized $Fe_3O_4$ nanoparticles, hence the term "ferrohydrogel". The terms "ferrogel" and "ferrohydrogel" are synonymous here. Because the ferroparticles are para- or superparamagnetic, the magnetic permeability, μ, of the ferrogel varies according to a function $\mu(h)=\mu_0+\mu_0+\Delta\mu(\theta_0 h_0/h)$, where $\theta_0$ is the loading (v/v) of ferroparticles in the initial hydrogel configuration, and $\mu_0$ is the permeability of free space, which also applies to the nonmagnetic structures above and below the ferrohydrogel. The inductance of the whole system, and hence and resonant frequency, will depend on h, μ(h), and the geometry and number of coil windings. Thus when the hydrogel swells or shrinks in response to a change in chemical concentration, thereby altering μ, h, and L, (the effect as depicted FIG. 2B—hydrogel 130 is much thinner than in FIG. 2A), and resonant frequency ($f_{res}$) changes in response thereto.

Figure 2C:
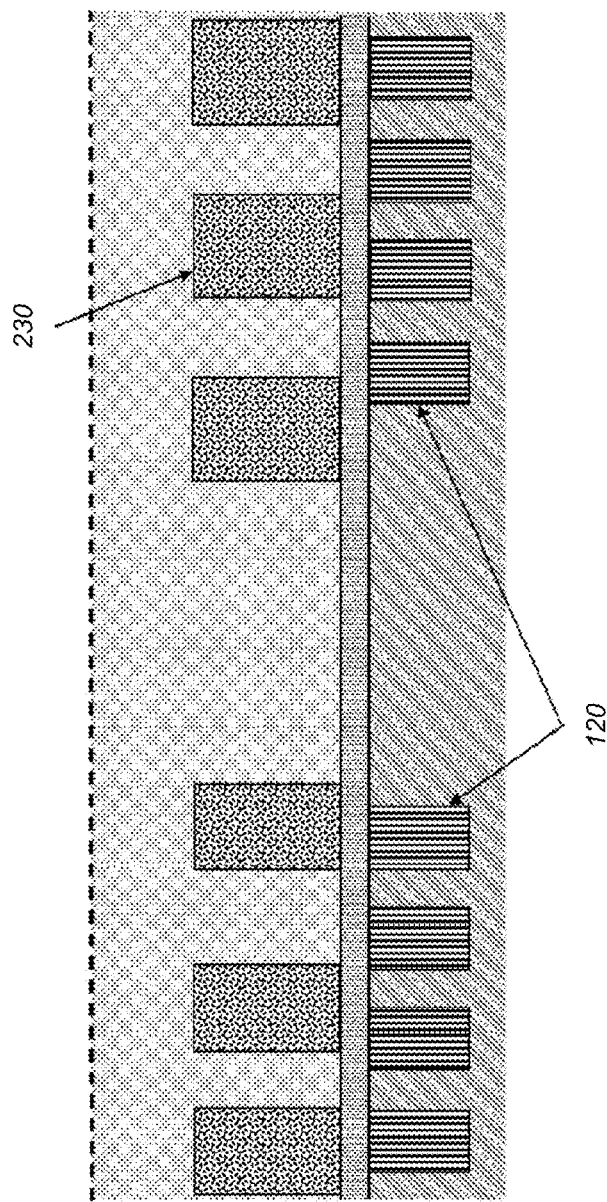
FIG. 2C is a cross-sectional schematic view of an alternative embodiment of the implantable device of FIG. 1A.

Referring to FIG. 2C, This changing-frequency effect also occurs if the ferrohydrogel 230 is patterned on the surface as an array of narrow columns, which can swell/shrink more rapidly than a flat sheet hydrogel of equal thickness (as depicted in FIG. 2C) would be able to. Hydrogels can also be made highly porous, thereby increasing mass transfer and hence speed of response. Thin cylindrical hydrogel columns are likely to swell and shrink more rapidly, as are porous hydrogels. Device coils 120 are as shown in FIG. 1A.

Figure 2D:
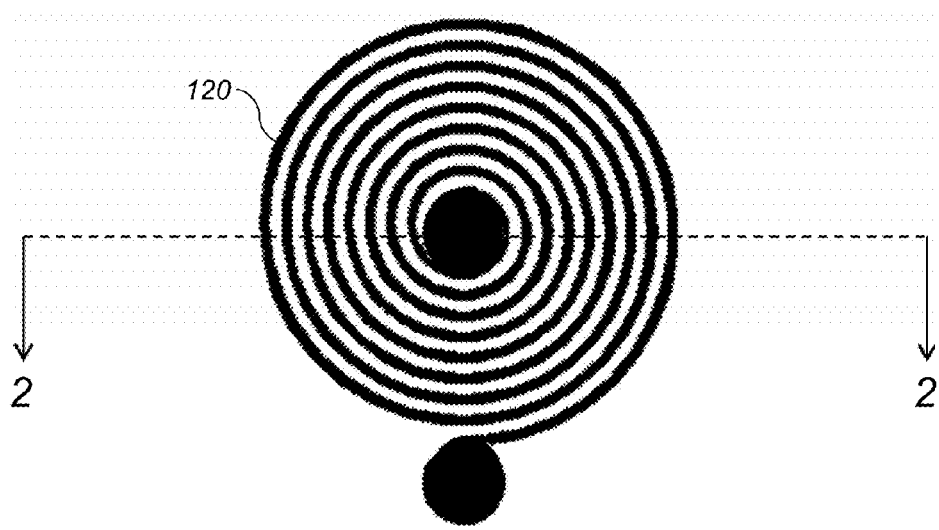
FIG. 2D is a top view of a device coil, a cross sectional view of which is depicted in FIG. 1A.

Referring to FIG. 2D, a top view of the device coils shown in previous schematics is provided. The reader should appreciate that the previous schematics, e.g., FIG. 1A, depict the device coil in a cross sectional view along line 2-2 shown in FIG. 2D. As shown in FIG. 2D, the terminals 220 of the device coil 120 are open (not mechanically connected to other components). The capacitance of the self-resonant circuit is the parasitic capacitance of the inductor coils themselves, as described above with respect to FIG. 1C, forming a parallel-resonant structure.

Magnetic permeabilities above and below the ferrohydrogel (as depicted in FIG. 2A) will be substantially constant and equal to permeability of free space, $\mu_0$. Magnetic permeability $\mu$ of the ferrohydrogel depends on volume fraction of inclusions, which decreases inversely with increasing h. Inductance L and hence resonant frequency are determined by $\mu$ and h.

The effects of h and $\mu(h)$ on L are due to magnetic polarization of the ferroparticles, which distorts the magnetic flux lines generated by the impinging electromagnetic field. Flux lines, currents, and inductances can be predicted, as a function of relevant parameters, using finite element multiphysics programs such as COMSOL™. Measured magnetic permeability of the ferrohydrogels at different swelling degrees can also be modeled by, for example, the Bruggeman effective medium equation.

Figure 3A:
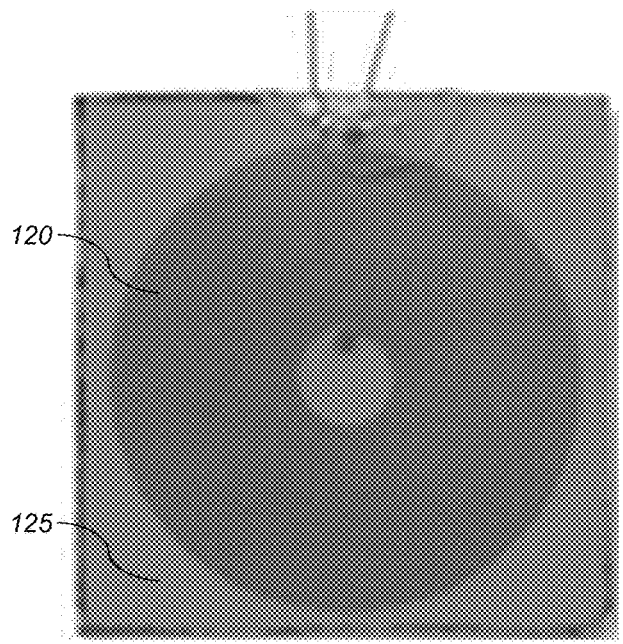
FIG. 3A is a representation of a photograph of a planar copper coil imbedded in insulating polyimide (PI) formed as a substrate.
Figure 3B:
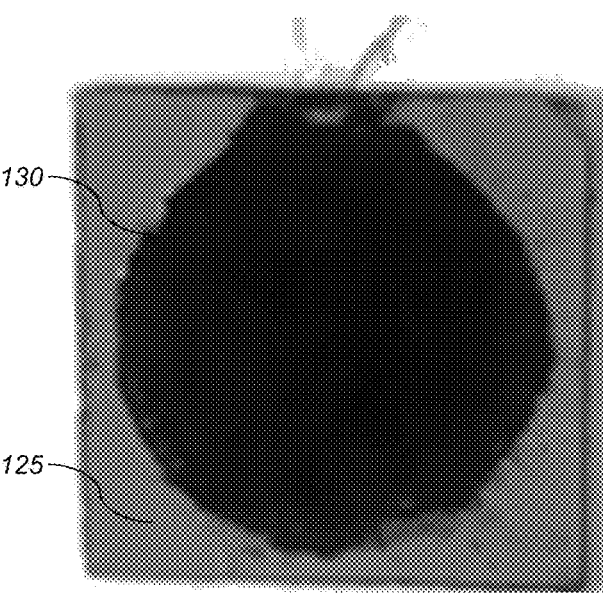
FIG. 3B is representation of a photograph of a ferrohydrogel layer bonded to the planar copper coil of FIG. 3A.

FIG. 3A shows a device coil 120 on a substrate 125. In a simple preliminary experiment, a planar copper coil imbedded in insulating polyimide (PI) formed the substrate (as depicted in FIG. 3A). FIG. 3B shows the ferrohydrogel 130 cured on top of the substrate 125. The ferrohydrogel included poly(methacrylic acid-co-acrylamide) (MAA/AAm, 10 mol % MAA) loaded with surfactant-coated 10 nm ferroparticles at 5% volume concentration. Thickness of the ferrogel was controlled by applying weight on top during polymerization. Ferrohydrogel was initially dried to ~50 μm thickness, and water was added on top in steps of 2 μl, causing stepwise swelling and increase in hydrogel thickness by ~6.5 μm/drop. Resonant frequency of the coil was recorded using an impedance analyzer.

Figure 3C:
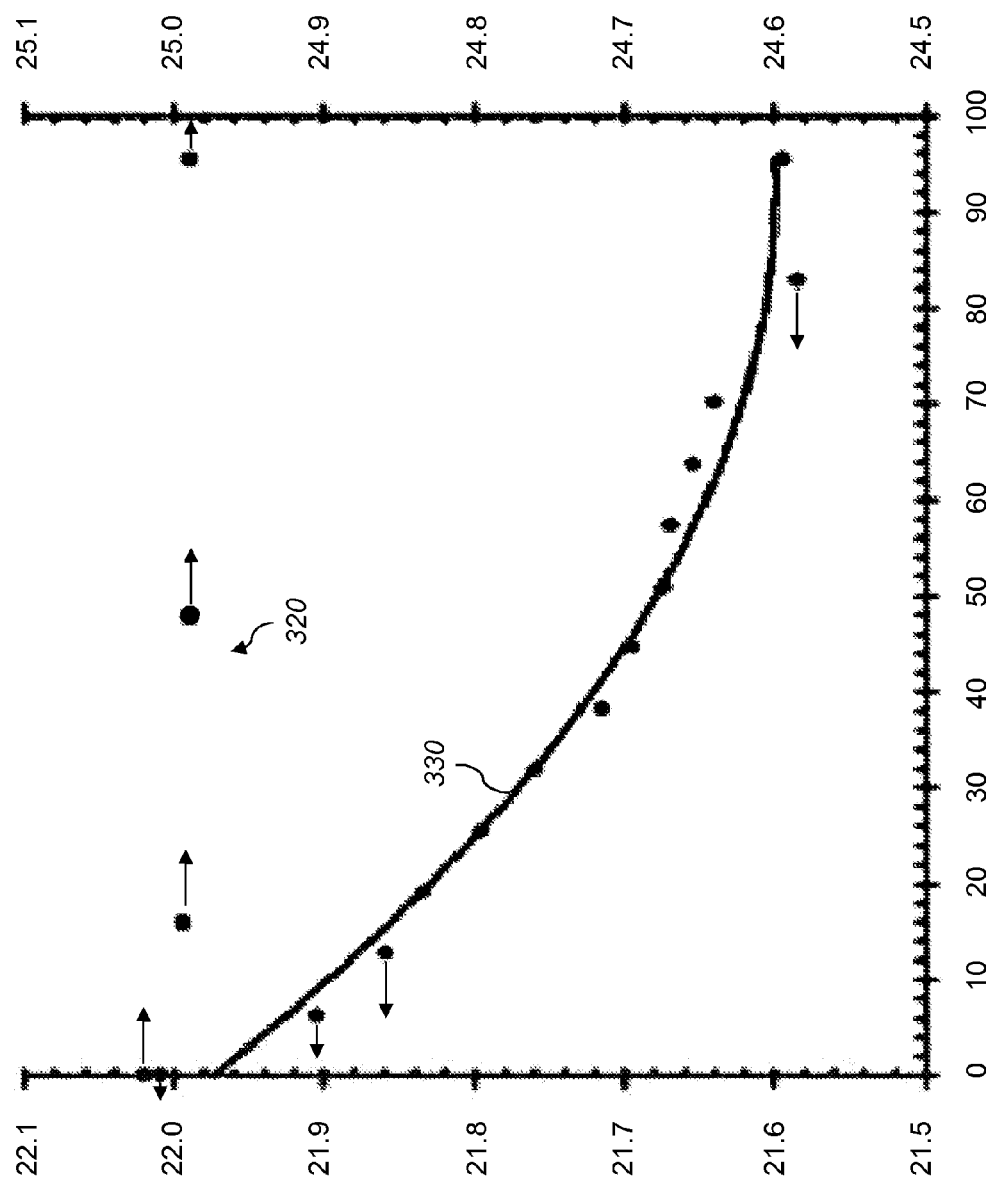
FIG. 3C is a graph of resonant frequency versus increase in thickness of the ferrogel over the coil assembly depicted in FIGS. 3A and 3B, and comparative data for a non-magnetically active hydrogel.

FIG. 3C shows the recorded $f_{res}$ plotted against estimated thickness of the gel. The abscissa is increase in thickness in μm. Each ordinate is resonant frequency in MHz. For the initial 50 μm thickness change, the sensitivity is about 5.6 kHz/μm, which can be detected by an impedance analyzer. The solid curve 330 represents a quadratic fit through the corresponding data points. Curve 330 and its data points correspond to the left ordinate (as indicated by the short arrows). A control hydrogel without ferroparticles did not exhibit any change in resonant frequency with swelling. This is shown by points 320, corresponding to the right ordinate (as indicated by the short arrows).

In a second experiment, latex beads consisting of $Fe_3O_4$ superparamagnetic nanoparticles, dispersed in a polystyrene matrix and coated with surfactant (ProMag™, Bangs Laboratories: 1 μm diameter), were suspended in an aqueous pregel solution containing poly (methacrylic acid-co-acrylamide) (MAA/AAm, 5 mol % MAA), crosslinker and initiator. The suspension was polymerized onto the substrate, producing a ferrohydrogel that completely covered the coil film, and bonded covalently to a GelBond® PAG sheet, trapping the coil. The ferrohydrogel was dried and determined to be approximately 20 μm thick in its dry state.

Following rehydration of the hydrogel, this construct was tested in aqueous buffers at varying pH values. Starting from "rest" at pH 4, where the hydrogel's charge density was low, the devices were exposed to solutions of progressively higher pH, charging the hydrogel and causing it to swell. The following shifts (as depicted in FIG. 3D) in resonant frequency were observed after exposure for 10 minutes: pH 5, $\Delta f_{res}$=0.05 MHz; pH 6, $\Delta_{res}$=0.07 MHz; pH 7, $\Delta f_{res}$=0.10 MHz; pH 12, $\Delta f_{res}$=0.186 MHz.

Figure 3D:
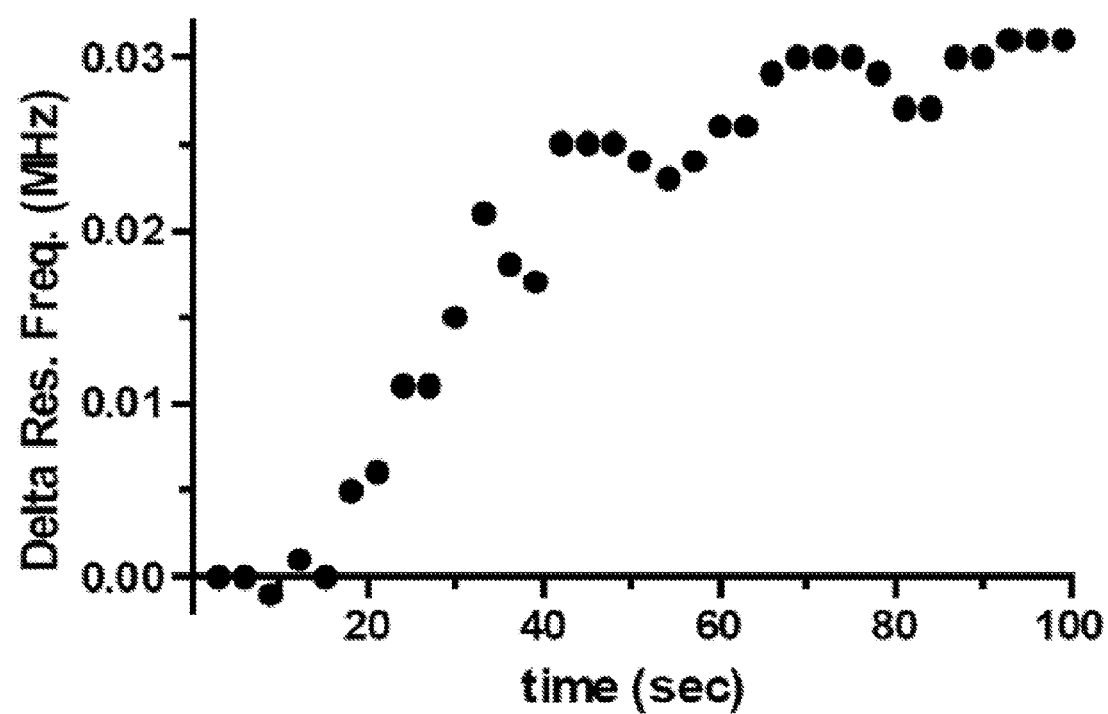
FIG. 3D is graph of change in natural frequency $\Delta f_{res}$ as a function of time.

FIG. 3D demonstrates rapid response, complete within ~70 sec, when the aqueous medium was step changed from pH 4 to pH 9. An initial "dead time" of 20 sec was observed. With increasing pH, the hydrogel swells, reducing the density of SPNs near the coil and hence magnetic permeability. Consequently, inductance decreases and resonant frequency increases. These results suggest that with further development, useful sensors can be produced using to SPN/hydrogel/microresonator approach.

The microsensor device depicted in FIGS. 1A and 2A includes a substrate that can be a commercially available plastic material such as polystyrene (PS), polymethylmethacrylate (PMMA), or polyimide (PI). PS is an attractive starting point since its glass transition temperature, $T_g$, is relatively low (~70° C.), enabling pressing operations with mild heating and cooling. A simple, batch preparation scheme carried out on a 4" diameter, 300-500 μm thick commercial polystyrene wafer, permits the fabrication of numerous devices in parallel, each of which can be about 1 $cm^2$ in diameter.

The process to fabricate the microsensor devices depicted in FIGS. 1A and 2A may include steps of patterning and electroplating gold (10-15 μm thick) device coils on the wafer surface, spin coating a 20 μm thick polystyrene layer on top, and covering the gold device coils to generate the sensor "base". An array of devices can be fabricated in parallel using common microfabrication techniques.

Following the generation of the base, under a suitable pattern mask, plasma-treated PS coating can be applied followed by creating free radicals on non-masked parts of the surface. Under the same mask, by photopolymerization, a thin (~50 μM thick) ferrohydrogel layer on activated surface can be generated. The recipe for the ferrohydrogel can be varied, by altering magnetic nanoparticle inclusion loading, monomers used, monomer concentrations, and crosslinker concentrations. Following polymerization, the hydrogel is temporarily dried down onto the base.

The next step is separating parallel devices by laser cutting. Then for each device, a laser-cut washer (W) of PS of, e.g., 100 μm thickness can serve as a "frame," which is heat pressed onto the base. A suitable membrane (M), such as Anopore™, is then cut and heat pressed on top of the frame. Finally, the device is moved into a vacuum chamber and the hydrogel chamber is filled with water by gravity feed though the top membrane.

A proof-of-concept microsensor can be generated which can involve thermo- and pH-sensitive hydrogels, such as poly(N-isopropylacrylamide) and poly(acrylamide-co-methacrylic acid), respectively. $Fe_3O_4$ nanoparticles can be incorporated either by covalently linking to the network through vinylized surfactant coatings, or suspended in latex beads that are physically entrapped in the hydrogel network, as described above. Structure of the ferronanoparticle/hydrogel composite can be determined by a transmission electron microscope (TEM).

Thin hydrogels can be synthesized anchored to the resonator, on the plasma activated surface, as described above. Swelling ($h/h_0$) of the hydrogels as a function of stimulus (temperature, T, or pH) can be monitored by profilometry and edge-on photography. At the same time, the RF impedance spectrum can be measured and $f_{res}$ can be determined. After a static correlation between $f_{res}$ and the established stimulus, kinetics of swelling and deswelling can be measured given repeated step changes in stimulus in both directions (increase and decrease in T or pH). With these experiments, effects of ferrohydrogel structure and geometry (thickness and surface patterning) on response time can be determined. For comparison, free swelling measurements can be carried out with bulk, unanchored ferrohydrogels. Completed devices, including the membrane, can then be assembled and the dynamic responses to changes in the external environment measured.

Following the steps that generated the base, the inductance, L, of the device coil and capacitance, C, of the base can be determined using a frequency analyzer and an external coil 111 (as depicted in FIG. 1B). Inductance and capacitance can be extracted from the high and low frequency parts of the impedance spectrum. In addition, internal resistance (R) can be determined from the quality factor, Q, of the resonance, defined as the ratio between resonant frequency of the device coil, $f_{res,coil}$, and the bandwidth of the resonance peak.

Figure 4A:
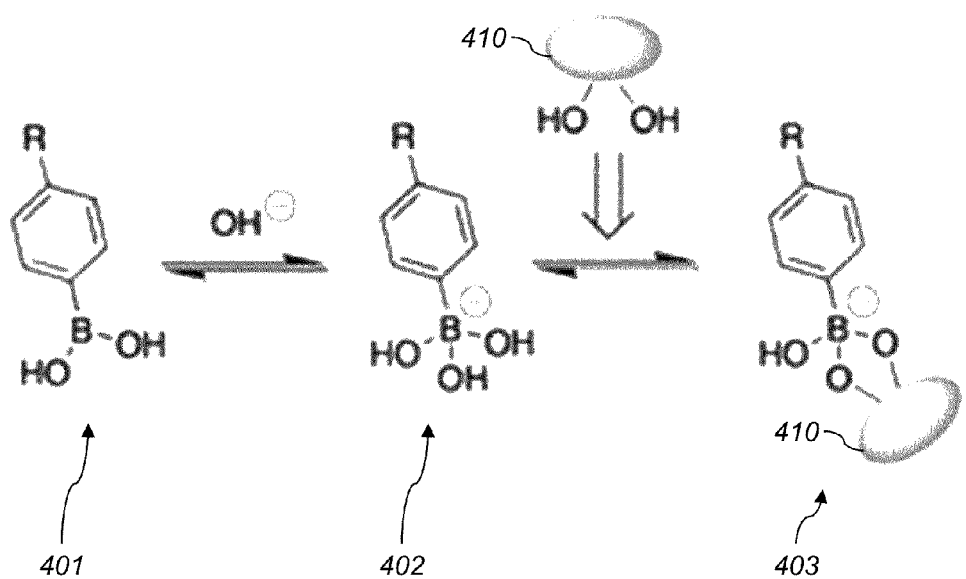
FIG. 4A depicts a mechanism by which a chemical environment forms a stable charged complex with phenylboronic acids (PBA).

Glucose concentration-sensitive sensors can be produced using glucose concentration-sensitive phenylboronic acid (PBA)-based ferrohydrogels. With respect to glucose sensing, some PBA-hydrogel systems advantageously do not use glucose oxidase. Other glucose-sensing hydrogel systems can use glucose oxidase. Different PBA derivatives can be generated and used in order to increase specificity of response to glucose. Copolymer hydrogels containing acrylamide (AAm) and methacrylamidophenylboronic acid (MPBA), at mole ratio 20/80 MBPA/AAm can be used. One role of AAm is to provide sufficient hydrophilicity to ensure swelling, while MPBA is the glucose sensitive moiety. MBPA, a Lewis acid, is ionized by complexation with $OH^-$, and the ionic form is stabilized in the presence of cis-diol containing molecules such as glucose (see FIG. 4A, mechanism by which glucose forms a stable charged complex with phenylboronic acids (PBA); here "R" refers to the copolymer chain to which PBA is attached). In its neutral, uncharged form 401, the hydroxyls around the boron atom are in a trigonal configuration, with very low binding affinity to sugars such as glucose. Upon binding an $OH^-$ ion ($pK_0$=8.86), PBA is converted to a charged form 402, with the OH groups in a tetragonal configuration. In this configuration, the boronate ion can form a bidentate condensation complex with the sugar molecule 410 through the latter's cis-diol. Complex formation is reversible. At pH 7.4 PBA is mostly uncharged, at low sugar concentrations. With increasing sugar concentration, however, the reaction is shifted to the right, and complexation stabilizes the charged configuration in charged form 403. This mechanism implies a sugar concentration-dependent change in acid-base properties, with apparent $pK_a=pK_0-\log_{10}(1+c_{sug}/K_{sug})$, where $c_{sug}$ is sugar concentration and $K_{sug}$ is the dissociation constant of the sugar with the charged boronate. Thus PBA is mostly uncharged at physiologic pH, but becomes more ionized with increasing sugar concentration.

Another consideration is the effect of pH on sensing (mechanism depicted in FIG. 4A), since diabetic individuals are prone to swings in blood pH, especially acidosis. The relative effects of pH or chemical concentration can be estimated in terms of the change in concentration needed to offset a change in pH, keeping the fraction ionized PBA, f, constant. A modified Henderson-Hasselbalch equation, $pH=pK_0-\log_{10}(1+c_{sug}/K_{sug})+\log_{10} f/(1-f)$ applies here: Setting $df=dpH+d\log_{10}(1+c_{sug}/K_{sug})=0$ it can be shown that $dc_g=-2.303(K_{sug}+c_{sug})dpH$. A shift of −0.1 pH units therefore offsets a ~3.2 mM increase in glucose concentration in the normoglycemic range. Accordingly, an independent means for tracking pH is needed with this sensing mechanism, which can be provided by a dual pH/glucose sensor, as described herein.

When the PBA moiety is incorporated into a polymer hydrogel, ionization leads to osmotic swelling forces. Under free swelling conditions, these forces can lead to substantial changes in hydrogel volume, which proceed until ionic swelling pressure is equalized by retractive pressures due to polymer elasticity and hydrophobic interactions between the hydrogel and the solvent. The balance of swelling forces is normally accounted for by Flory-Rehner-Donnan-Langmuir (FRDL) theory, which under free swelling conditions predicts $$\ln(1-\phi)+\phi+\chi\phi^2+\rho_0 \bar{v}_w[(\phi/\phi_0)^{1/3}-(\phi/2\phi_0)]-\bar{v}_w c_s(\lambda+1/\lambda-2)=0$$

where $\phi$ is the volume fraction of polymer at equilibrium, $\phi_0$ is the volume fraction of polymer at synthesis, $\rho_0$ is proportional to the crosslink density at synthesis, $\bar{v}_w$ is the partial molar volume of water (0.018 L/mol), $c_s$ is the salt concentration in the external solution (typically 0.155 mM), and $\chi$ is the Flory interaction parameter. The swelling ratio relative to synthesis is given by $Q=\phi_0/\phi$. The term $\lambda$ is the Donnan ratio, determined by properly assuming electroneutrality in the hydrogel:

$$(1-\phi)c_s(\lambda-1/\lambda)-f\sigma_0(\phi/\phi_0)=0$$

where $\sigma_0$ is the density (mol/volume of hydrogel) of ionizable PBA units at synthesis, and f is the fraction of these units that are ionized at a given pH and fructose concentration. Taking into account that pH inside the hydrogel differs from that in the external solution, the Donnan ratio figures into the expression for f according to $$f = \frac{1}{1+\lambda 10^{-(pH-pK_0)}/(1+c_{sug}/K_{sug})}$$

Combining the above equations enables prediction of swelling pressure under confinement, or degree of free swelling when the hydrogel is unconfined and $\Delta P=0$.

Free swelling experiments have been undertaken to ascertain the validity of the FRDL theory and to obtain parameter estimates. To this end, hydrogels were synthesized from a pregel solution containing 20 mol % MPBA and 80 mol % AAm, crosslinked with 10 mg N, N-methylene-bisacylamide (BIS), all dissolved in 1 mL of 1N NaOH along with ammonium persulfate (initiator) and N,N,N,N-tetramethylethylenediamine (TEMED, accelerator). Copolymerization with AAm was undertaken since MPBA is intrinsically hydrophobic.

Figure 4B:
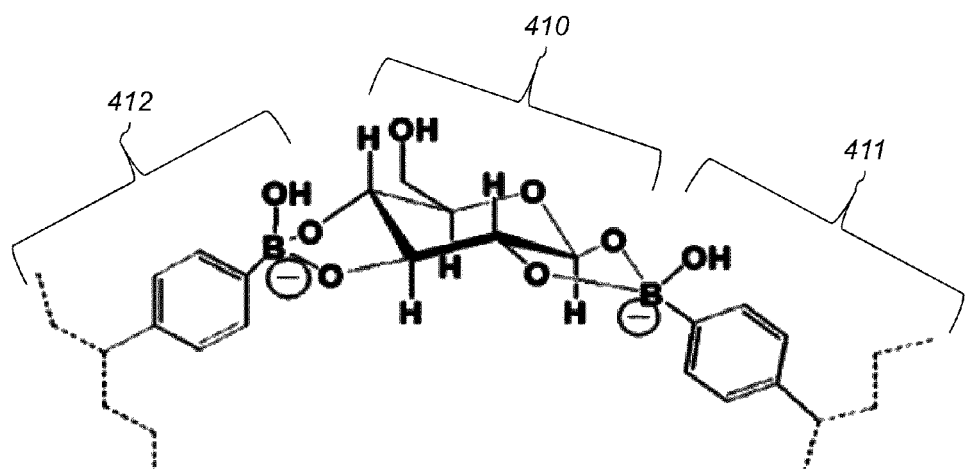
FIG. 4B is a diagram of when PBA moieties are highly charged, where a single glucose molecule can complex with two PBAs, forming transient crosslinks between host polymer chains.

Fructose responsive swelling was first studied since it is simpler than glucose responsive swelling. FIG. 4D displays free swelling equilibria in buffered saline solutions ($c_s$=0.155 mM) over an extensive pH range and for fructose concentrations 0, 0.5, 2, 7, and 20 mM. The abscissa is pH and the ordinate is gel thickness in mm. Swelling increases sigmoidally with pH, and exhibits shifts in the acid direction with increasing fructose concentration. Curves are fits of FRDL theory (free swelling: $\Delta P=0$), based on $\chi=(1-f)\chi_u+f\chi_c$, where "u" and "c" refer to the uncharged and uncharged forms of MPBA, respectively. A potential rationale for ionization-dependent $\chi$ lies in the change in polarity and hence hydrophilicity of the PBA moiety when it is charged.23 The parameters $\rho_0$ and $\sigma_0$ were fixed at synthesis, and least squares fitting yielded the parameter estimates $\chi_m$=0.61, $\chi_c$=0.35, $\rho_0$=0.028, and $K_f$=0.10 mM. The difference between $\chi_u$ and $\chi_c$ is large; these values bracket $\chi$=0.5, the critical value demarcating the transition between hydrophilicity and hydrophobicity.

In contrast to fructose, glucose contains two cis-diols, and when the hydrogel is sufficiently ionized at high pH, glucose forms transient bridges, or crosslinks between MPBA's on separate polymer chains (see FIG. 4B, when PBA moieties are highly charged, a single glucose molecule 410 can complex with two PBAs 411, 412, forming transient cross-links between host polymer chains), causing the hydrogel to shrink. These two opposing effects are manifested in the joint pH-glucose swelling characteristic illustrated in FIG. 4C (graph of hydrogel diameter (ordinate, mm) versus pH (abscissa) depicting joint effect of pH and glucose concentration $C_G$ on hydrogel swelling, reflecting these effects). Below about pH 8.6, increased glucose concentration leads to increased swelling, while above about pH 8.6, increased glucose concentration causes the hydrogel to shrink.

Figure 4C:
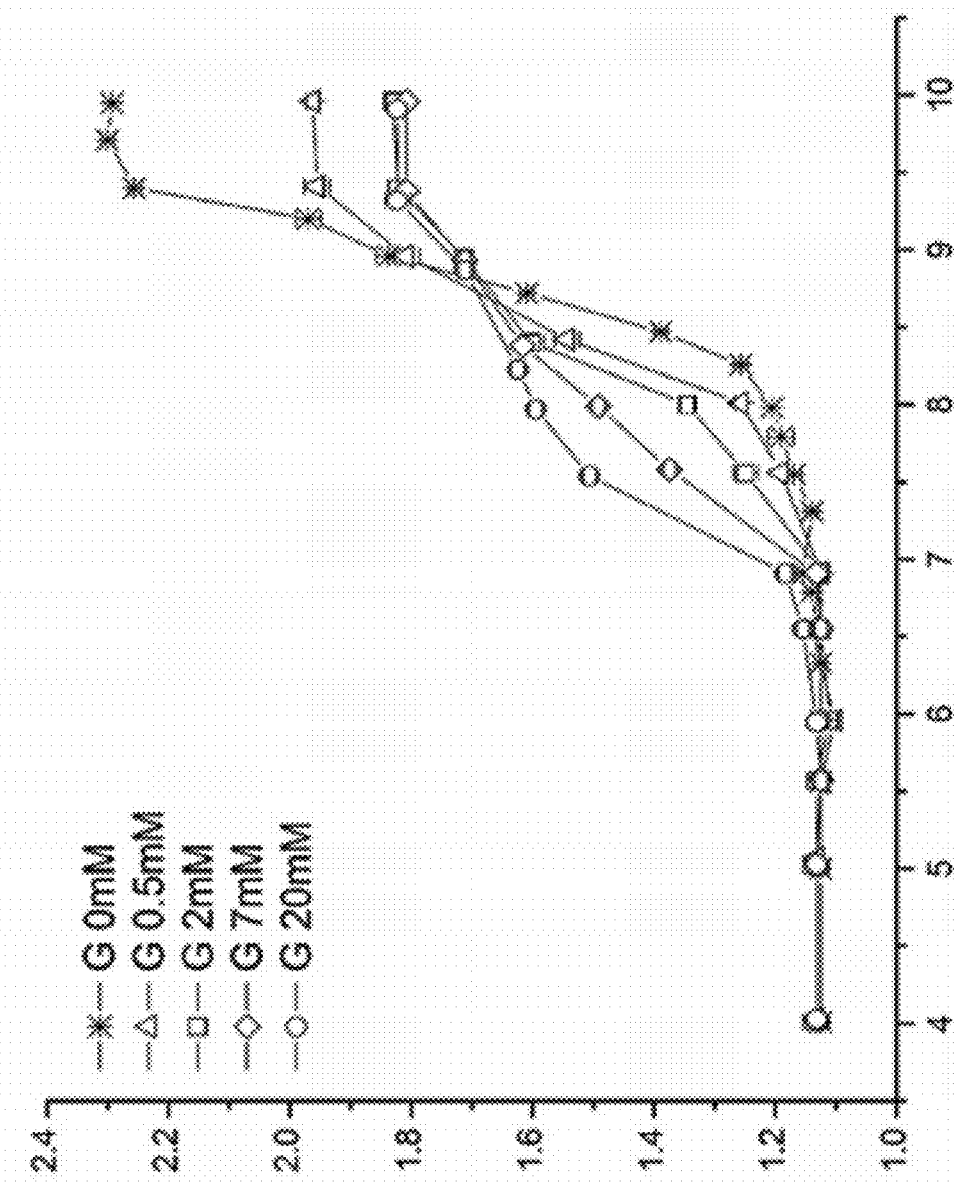
FIG. 4C is a diagram of effect of pH and glucose concentration on ferrohydrogel swelling expressed as ferrohydrogel diameter in mm versus pH.
Figure 4D:
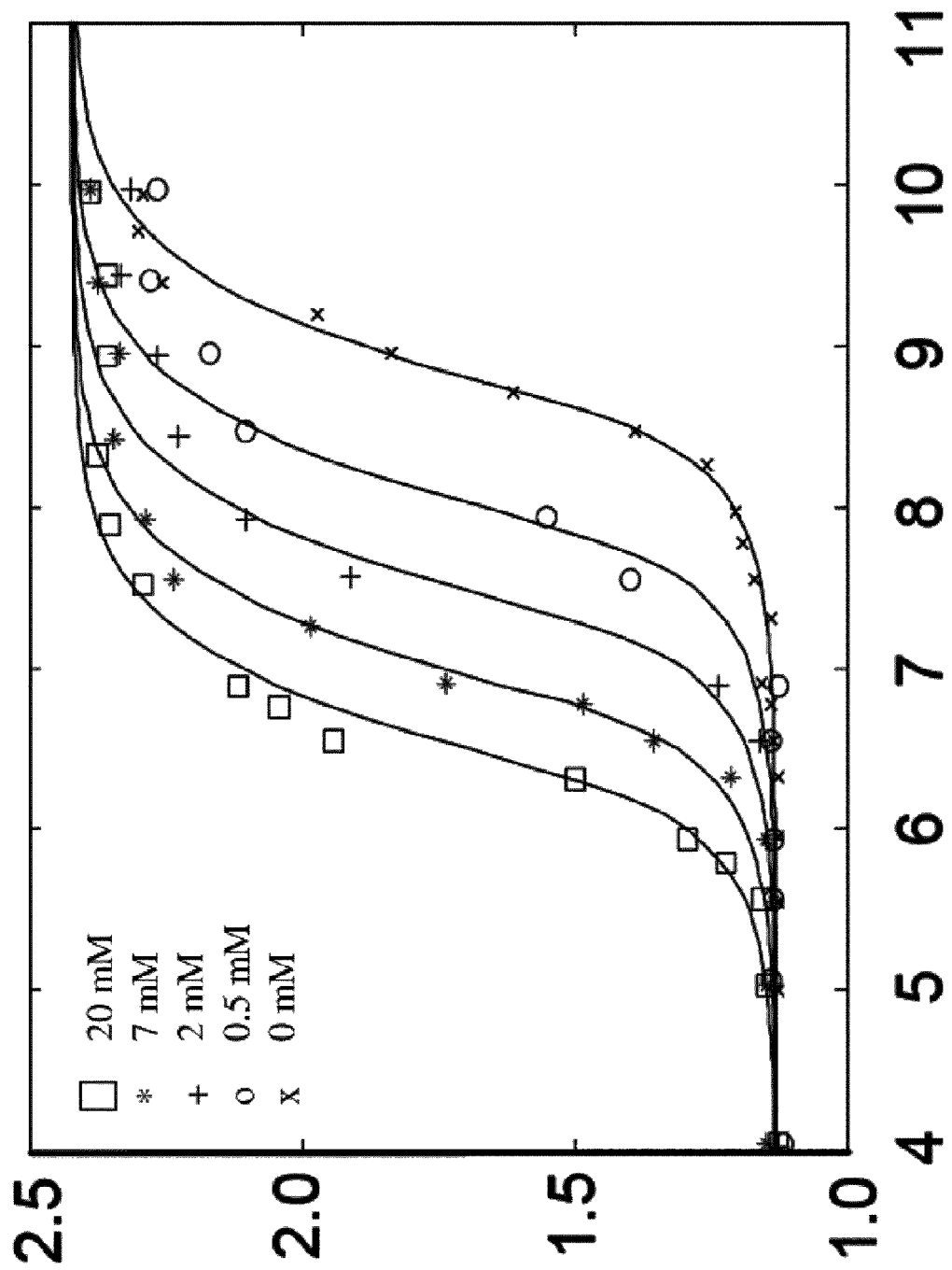
FIG. 4D is a graph of swelling diameter as a function of pH for various fructose concentrations.
Figure 5:
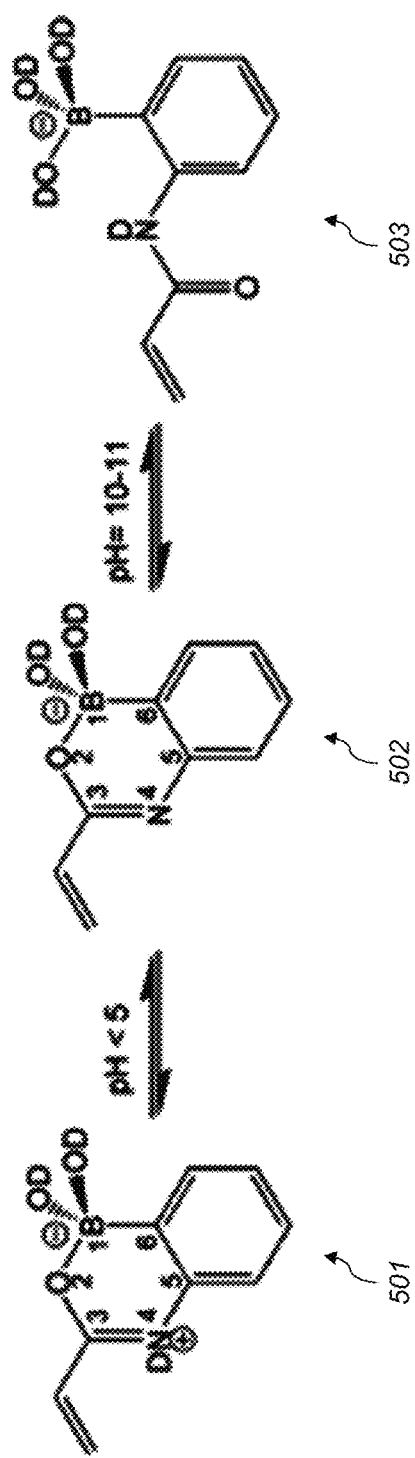
FIG. 5 is a diagram of structure and acid-base properties of the monomer 2-acrylamidophenylboronate (2-APB).

It is apparent from FIG. 4C that swelling is sensitive to pH near pH 7.4, which is a disadvantage, particularly given the tendency towards acidosis and alkalosis in diabetes. It has been demonstrated that shrinking near pH 7.4 is partially, but not completely eliminated by co-incorporating dimethylaminopropyl-methacrylamide (DMP), at equimolar amounts with MPBA, in the hydrogel. DMP is a Lewis base which replaces OH⁻ in the reaction scheme of FIG. 4A.

pH-sensitivity can be effectively eliminated by repositioning the boronate on the phenyl ring, converting MPBA to another glucose sensitive monomer, 2-acrylamidophenylboronate (2-APB). The structure of this monomer and its acid-base reactions are shown in FIG. 5. For pH 5-9, the dominant form 502 contains an intramolecular Lewis acid-base complex, with essentially pH-independent shrinking as a function of glucose concentration, along with effective specificity against potentially interfering species, e.g., lactate. Below pH 5, the nitrogen atom in 2-APB is ionized by binding of a free proton (shown as a deuteron, D, in form 501) while at pH>10 the boron atom, B, in 2-APB is complexed with hydryoxide ion (shown as OD in form 503), and the intramolecular ring containing boron is broken. The forms and reactions described in this paragraph are commonly known in the art.

To synthesize chemically sensitive PBA-based hydrogels, first ferrohydrogels can be synthesized and their chemical concentration dependent swelling properties measured. The concentration dependent swelling properties can be based on changes in glucose, pH, and other chemical environments as discussed herein. Next, 2-APB/AAm hydrogels can be synthesized and characterized, measuring the concentration-dependent swelling equilbria and kinetics, first without and then with the ferromagnetic nanoparticles. Swelling or shrinking kinetics can be measured at 20° C. (room temperature) and 37° C., since the latter is body temperature, and since others have demonstrated a strong accelerating temperature effect on binding/dissociation kinetics of PBA with glucose.

Next, devices containing hydrogels sensitive to glucose or other chemicals can be assembled and tested, combining methods already outlined above. Device response kinetics can be tested with step changes in glucose concentration at relevant levels at over the pH range 7.1-7.5, relevant to acidosis and alkalosis, and can also check sensitivity to glucose over interfering species such as fructose and lactate.

In a situation where the function of pancreatic β-cells is to be provided, as well as many other situations, blood glucose level may need to be sensed on a continuous basis so that insulin can then be delivered when the patient is hyperglycemic. In addition, low basal insulin can be delivered during normoglycemic periods. In various examples of insulin pumps and glucose monitors, when the device senses a glucose level nearing hypoglycemia, it can either signal a temporary halt to insulin delivery, or suggest the patient restore normoglycemia by ingesting carbohydrates. An example of a continuous glucose monitoring system with insulin pump is the MEDTRONIC MINIMED PARADIGM REAL-TIME REVEL System. However, this system requires a sensor that extends on both sides of the skin for monitoring. Various aspects described herein provide improved blood glucose sensors that can provide accurate measurements and do not require leaving a needle through the skin for extended periods of time.

Figure 6A:
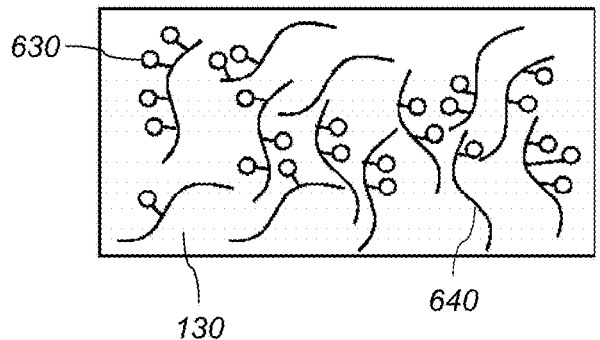
FIGS. 6A, 6B, and 6C are diagrams of various hydrogel structures, each having a different type of ferromagnetic particle structure embedded therein.
Figure 6B:
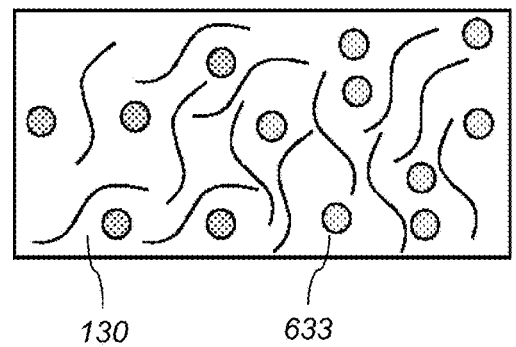
Figure 6C:
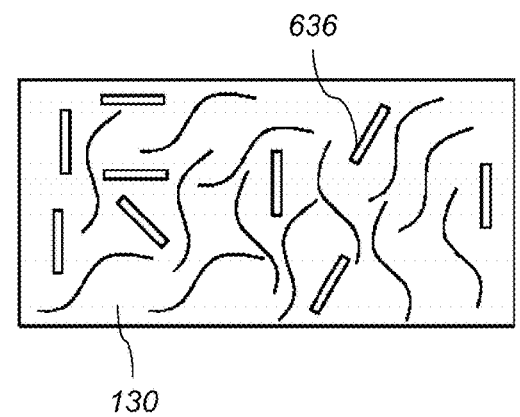

Referring to FIGS. 6A through 6C, various embodiments for embedding ferromagnetic particles and structures in the hydrogel 130, as discussed herein, are provided. For example, in FIG. 6A, ferromagnetic nanoparticles 630 are bonded to polymer chains 640 that form the hydrogel. As discussed above, the polymer chains 640 can be crosslinked to form a mesh or other crosslinked configuration. In FIG. 6B, micron-sized structures 633 filled with ferromagnetic nanoparticles can be dispersed within the hydrogel 130. In FIG. 6C, ferromagnetic particles 636 in the form of plates, bars, or flakes can be distributed throughout the hydrogel 130. It should be appreciated that ferromagnetic particles discussed herein can be magnetic, ferromagnetic, paramagnetic, or superparamagnetic.

Figure 7:
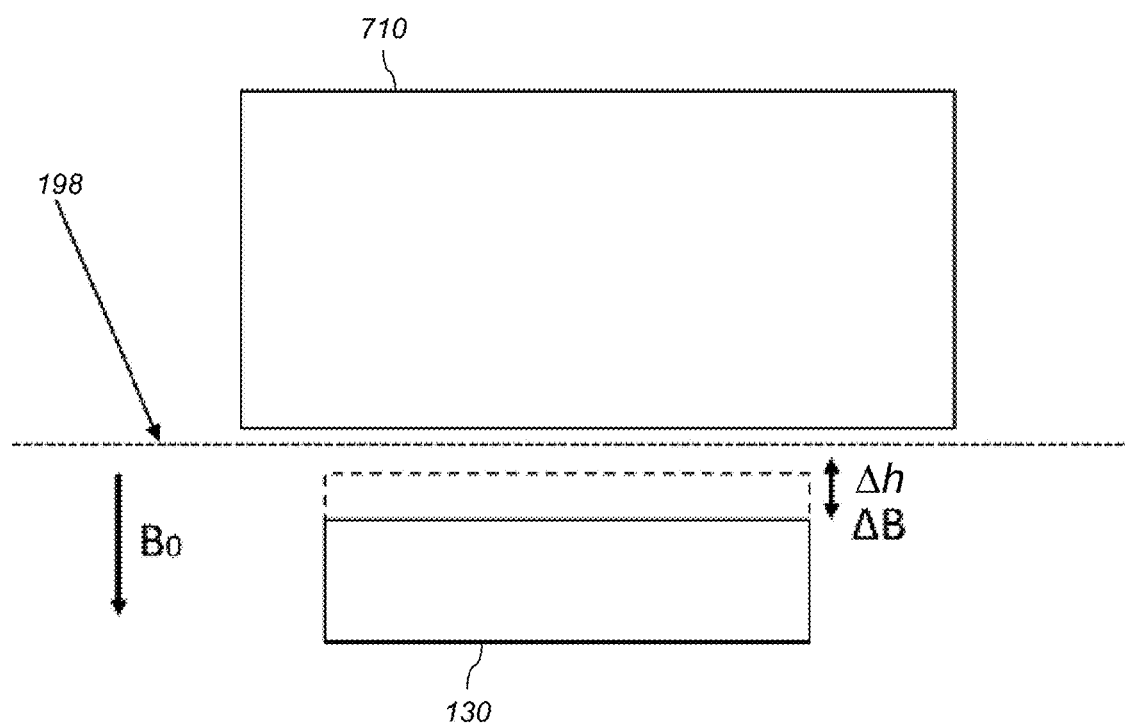
FIG. 7 is an alternative embodiment of a sensing system using a Hall-effect type sensor.

Referring to FIG. 7, an alternative embodiment is depicted, as described above, where a Hall-effect type sensor 710 is used in association with an implantable device having magnetic nanoparticles. In this embodiment, a sensitive magnetic sensor can be used to establish a bias field $B_0$. Changes in the height of the hydrogel layer can result in changes in the magnetic field identified as ΔB. Total field (B) is then $B_0$+ΔB. By sensing the overall field (B), changes in the field (i.e., ΔB) can be measured. The magnitude of ΔB can then be correlated to changes in the height of the hydrogel which can then be correlated to the concentration of chemicals for which the hydrogel is provided. As shown in FIG. 7, the magnetic-field sensor 710 can be spaced apart from the hydrogel 130, e.g., outside the skin when the hydrogel is implanted in the body. The magnetic field sensor is also referred to as a "magnetic-field detector" to differentiate it from the implantable device, which is sometimes referred to herein as a "sensor" since it senses the condition. In other examples, a SQUID can be used as the magnetic-field detector. SQUID detectors measure electrical properties resulting from the effects of magnetic fields on currents through Josephson junctions.

Figure 8A:
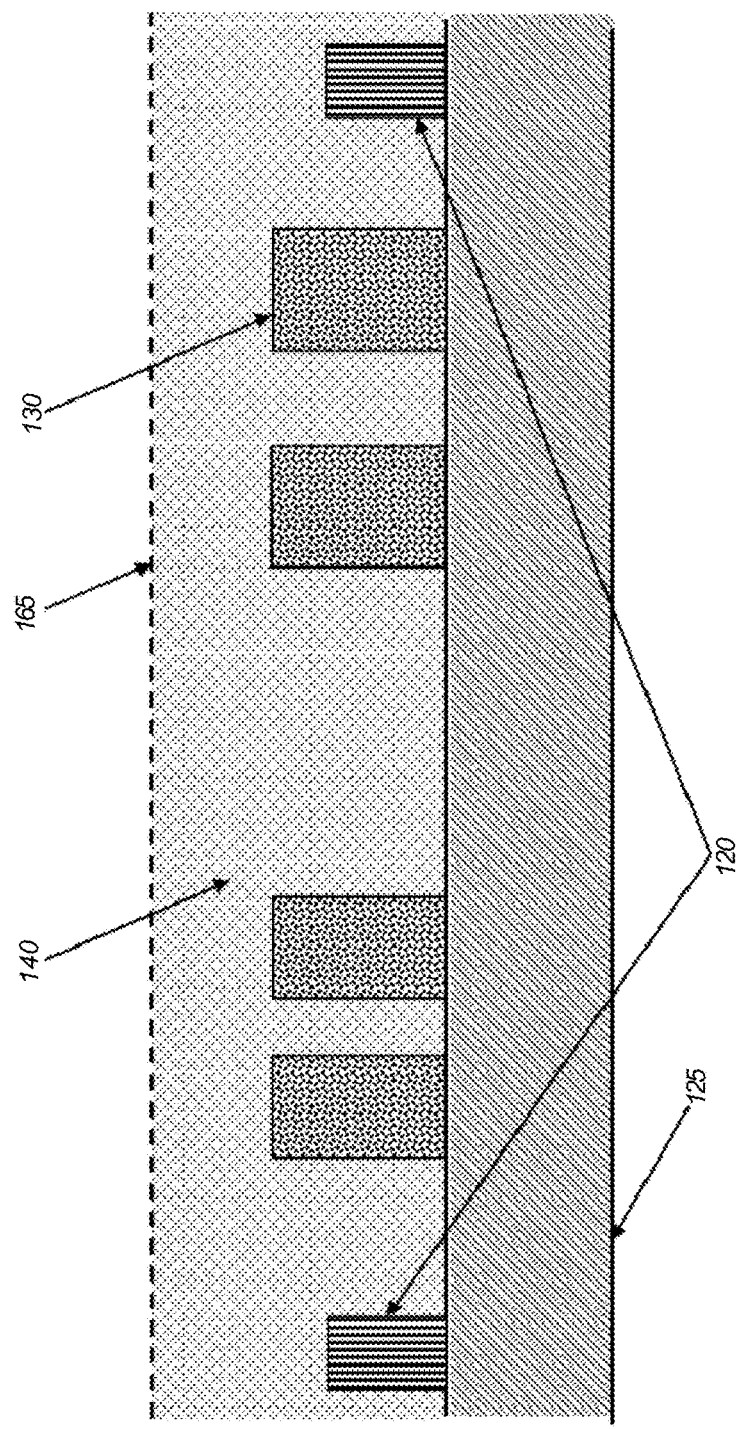
FIGS. 8A and 8B are alternative embodiments of the implantable device having various coil-hydrogel structures.
Figure 8B:
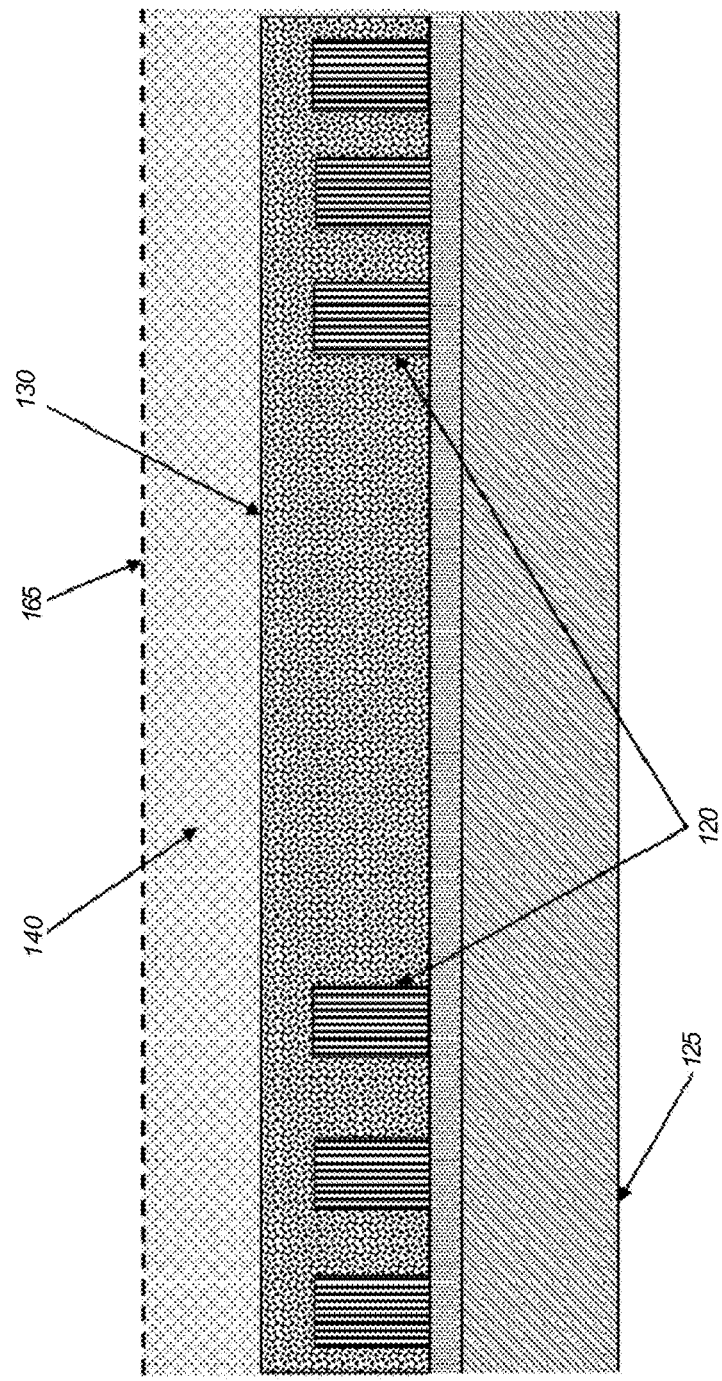

Referring to FIGS. 8A and 8B, various embodiments similar to that depicted in FIG. 1 are provided. In FIG. 8A, device coils 120 are depicted as being positioned above the substrate 125 and inside the fluid space 140 (i.e., the space defined by the membrane 165 which selectively allows passage of fluid, e.g., intercellular fluid, and prevents passage of particles of predetermined sizes, e.g., cells). Also depicted are patterns of the hydrogel 130. In this embodiment, the device coils are electrically insulated from the surrounding to prevent electrical shorting. In FIG. 8B, similar to FIG. 8A, the insulated device coils 120 are positioned above the substrate 125, however, the device coils are positioned inside the hydrogel 130.

Figure 9A:
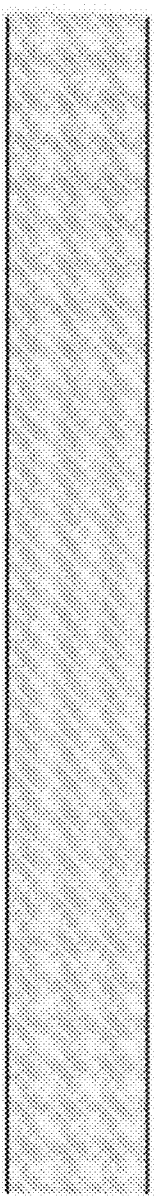
FIGS. 9A, 9B, and 9C are diagrams showing various fabrication steps according to various aspects.
Figure 9B:
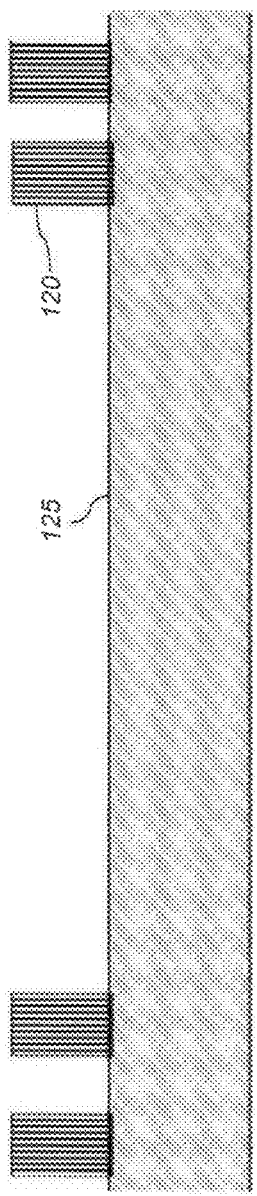
Figure 9C:
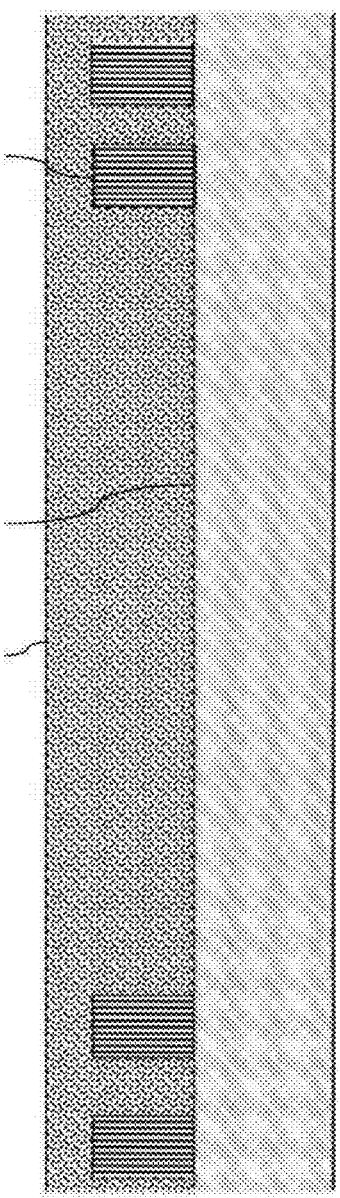

Referring to FIGS. 9A through 9C, process steps are presented for fabricating various embodiments of the microsensor according to the various aspects. FIG. 9A depicts a starting substrate, e.g., silicon, glass, plastic, insulated metal layer, or other commonly used substrates in the field of semiconductors. FIG. 9B depicts formation of device coils 120 over the substrate 125 using metal deposition, patterning, and electroplating. FIG. 9C depicts formation of the hydrogel 130 over the substrate 120 after the surfaces are treated with adhesion promoters. The hydrogel can be cast-formed.

Figure 10:
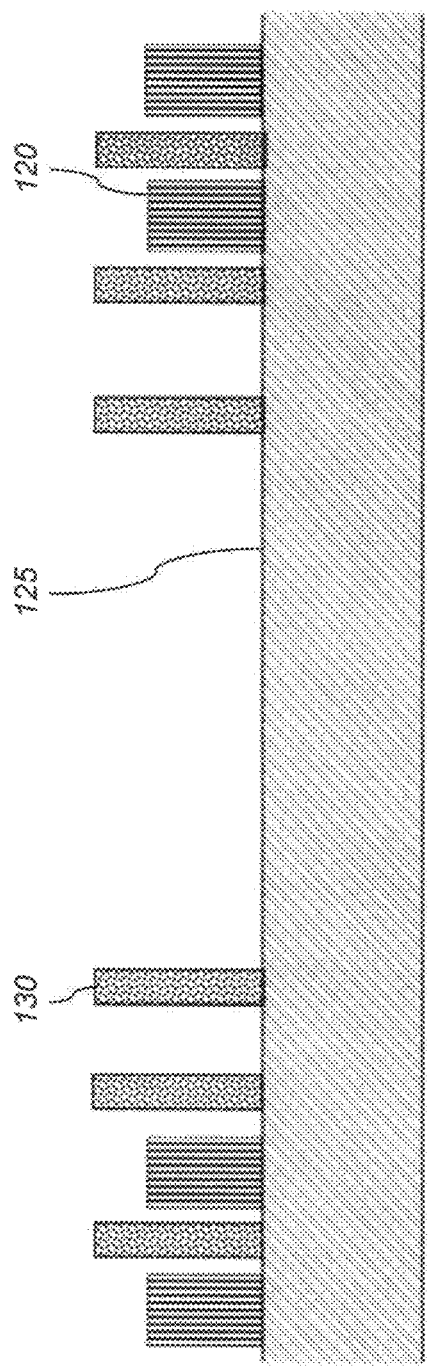
FIG. 10 shows various embodiments of hydrogel structures.

FIG. 10 depicts various patterns of the hydrogel 130 formed about the device coils 120. These patterns can be formed individually, or formed by a masking process after formation according to FIG. 9C. Other approaches (not shown) include formation of the device coils inside of the substrate followed by formation of the hydrogel over the substrate are also envisioned. The ring 155 shown in FIG. 1A can be made from the same material as the substrate and bonded thereto. Alternatively, the ring can be made as an integral part of the substrate.

Figure 11:
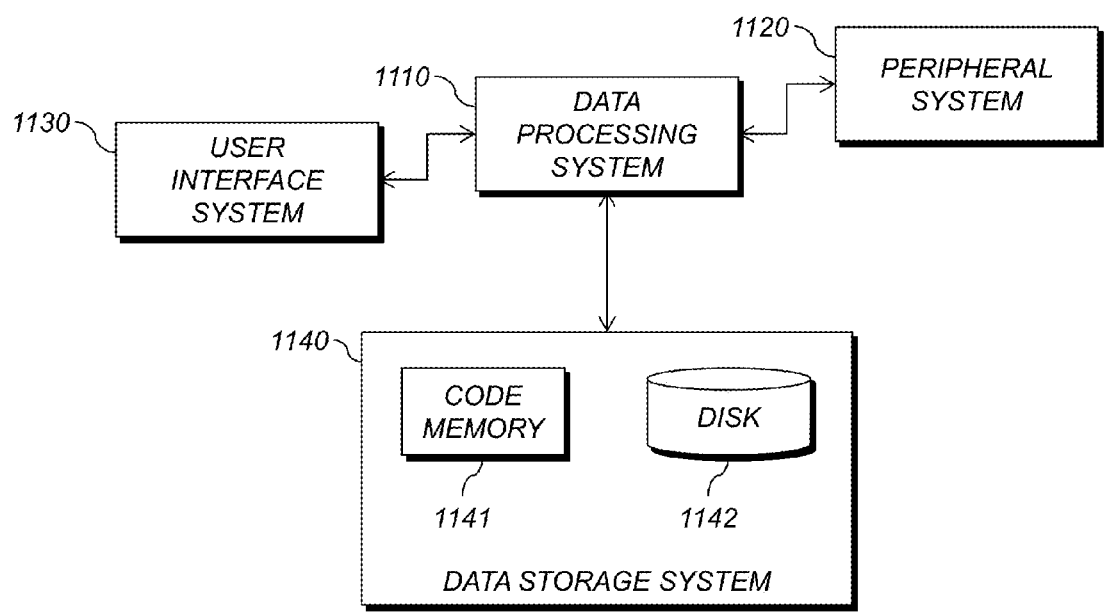
FIG. 11 is a high-level diagram showing the components of a data-processing system.

FIG. 11 is a high-level diagram showing the components of a data-processing system for analyzing data and performing other analyses described herein, e.g., detecting resonance frequencies. The system includes a data processing system 1110, a peripheral system 1120, a user interface system 1130, and a data storage system 1140. The peripheral system 1120, the user interface system 1130 and the data storage system 1140 are communicatively connected to the data processing system 1110. Data processing system 1110 can be communicatively connected to a network, e.g., the Internet or an X.25 network.

The data processing system 1110 includes one or more data processor(s) that implement processes of various aspects described herein. A "data processor" is a device for automatically operating on data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 1120, user interface system 1130, and data storage system 1140 are shown separately from the data processing system 1110 but can be stored completely or partially within the data processing system 1110.

The data storage system 1140 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to data processing system 1110 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 1110 to perform a particular series of operational steps when loaded, thereby implementing functions or acts specified herein.

In an example, data storage system 1140 includes code memory 1141, e.g., a random-access memory, and disk 1142, e.g., a tangible computer-readable rotational storage device such as a hard drive. Computer program instructions are read into code memory 1141 from disk 1142, or a wireless, wired, optical fiber, or other connection. Data processing system 1110 then executes one or more sequences of the computer program instructions loaded into code memory 1141, as a result performing process steps described herein. In this way, data processing system 1110 carries out a computer implemented process. For example, blocks of the flowchart illustrations or block diagrams herein, and combinations of those, can be implemented by computer program instructions.

Computer program code can be written in any combination of one or more programming languages, e.g., Java, Smalltalk, C++, C, or an appropriate assembly language. Program code to carry out methods described herein can execute entirely on a single data processing system 1110 or on multiple communicatively-connected data processing systems 1110. For example, code can execute wholly or partly on a user's computer and wholly or partly on a remote computer, e.g., a server. The remote computer can be connected to the user's computer through a network. The user's computer or the remote computer can be non-portable computers, such as conventional desktop personal computers (PCs), or can be portable computers such as tablets, cellular telephones, smartphones, or laptops.

The peripheral system 1120 can include one or more devices configured to provide data to the data processing system 1110. For example, the peripheral system 1120 can include a reader, e.g., as shown in FIGS. 1A and 1B. The data processing system 1110, upon receipt of data from a device in the peripheral system 1120, can store such data in the data storage system 1140.

The user interface system 1130 can include a mouse, a keyboard, another computer (connected, e.g., via a network or a null-modem cable), or any device or combination of devices from which data is input to the data processing system 1110. In this regard, although the peripheral system 1120 is shown separately from the user interface system 1130, the peripheral system 1120 can be included as part of the user interface system 1130.

The user interface system 1130 also can include a display device, a processor-accessible memory, or any device or combination of devices to which data is output by the data processing system 1110. In this regard, if the user interface system 1130 includes a processor-accessible memory, such memory can be part of the data storage system 1140 even though the user interface system 1130 and the data storage system 1140 are shown separately in FIG. 11.

In view of the foregoing, various embodiments of the invention measure the magnetic properties of sensors. A technical effect is to determine, e.g., the resonant frequency of a hydrogel-device coil sensor. In an example, reader 110 (FIG. 1A) includes a data processing system 1110 and other components shown in FIG. 11, and data processing system 1110 executes stored program code to cause interrogation of the microsensor and determination of its resonant frequency or other electrical characteristics, as described herein.

Figure 13:
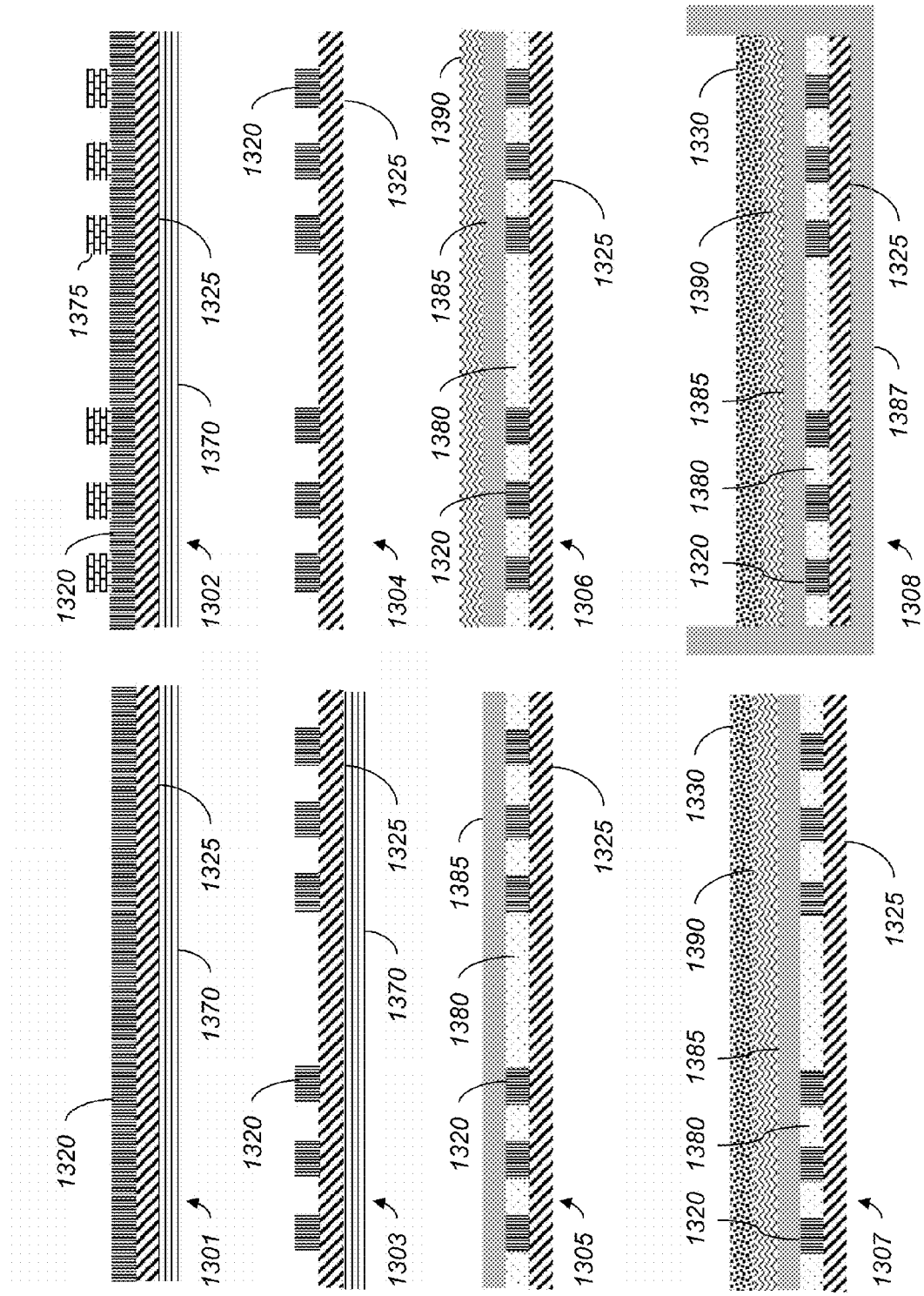
FIG. 13 shows steps in an exemplary fabrication process for ferrogel sensors.

FIG. 13 shows steps in an exemplary fabrication process for ferrogel sensors. In view 1301, copper 1320 is deposited over polyimide 1325 on a silicon backer 1370. In view 1302, photoresist 1375 is deposited on copper 1320. After etching copper 1320 and removing photoresist 1375, the result is device coil 1320, shown in view 1303. View 1304 shows the silicon backer having been removed. In an example, a planar coil (L=2.1 μH, outer diameter=10 mm, 20 turns) was patterned on a polyimide copper-clad laminate sheet. In view 1305, ultraviolet-curable epoxy 1380 is applied to the polyimide 1325 to attach transparency film 1385 to the top of the coil 1320. This provides electrical passivation. View 1306 shows gel-support layer 1390, e.g., GELBOND, applied over transparency film 1385. View 1307 shows hydrogel 1330 cast on gel-support layer 1390. In order to form the pH-sensitive poly (MAA-co-AAm) ferrogel, SPNs in PS beads of 1 μm diameter were sonicated at 3 vol % for 1 hr in an aqueous pregel solution containing MAA, AAm, methylenebisacrylamide (crosslinker) and tetraethylmethylenediamine (accelerator). The initiator, ammonium persulfate, was then added and the mixture was cast (20 μm thick) on a bonding layer (GELBOND). The result was a ferrogel pH sensor, with dimension 1.5 cm×1.5 cm×0.5 mm. View 1308 shows the sensor attached into a chamber made out of a laser machined polymeric film 1387, which can be the same polymer as film 1385.

Figure 14:
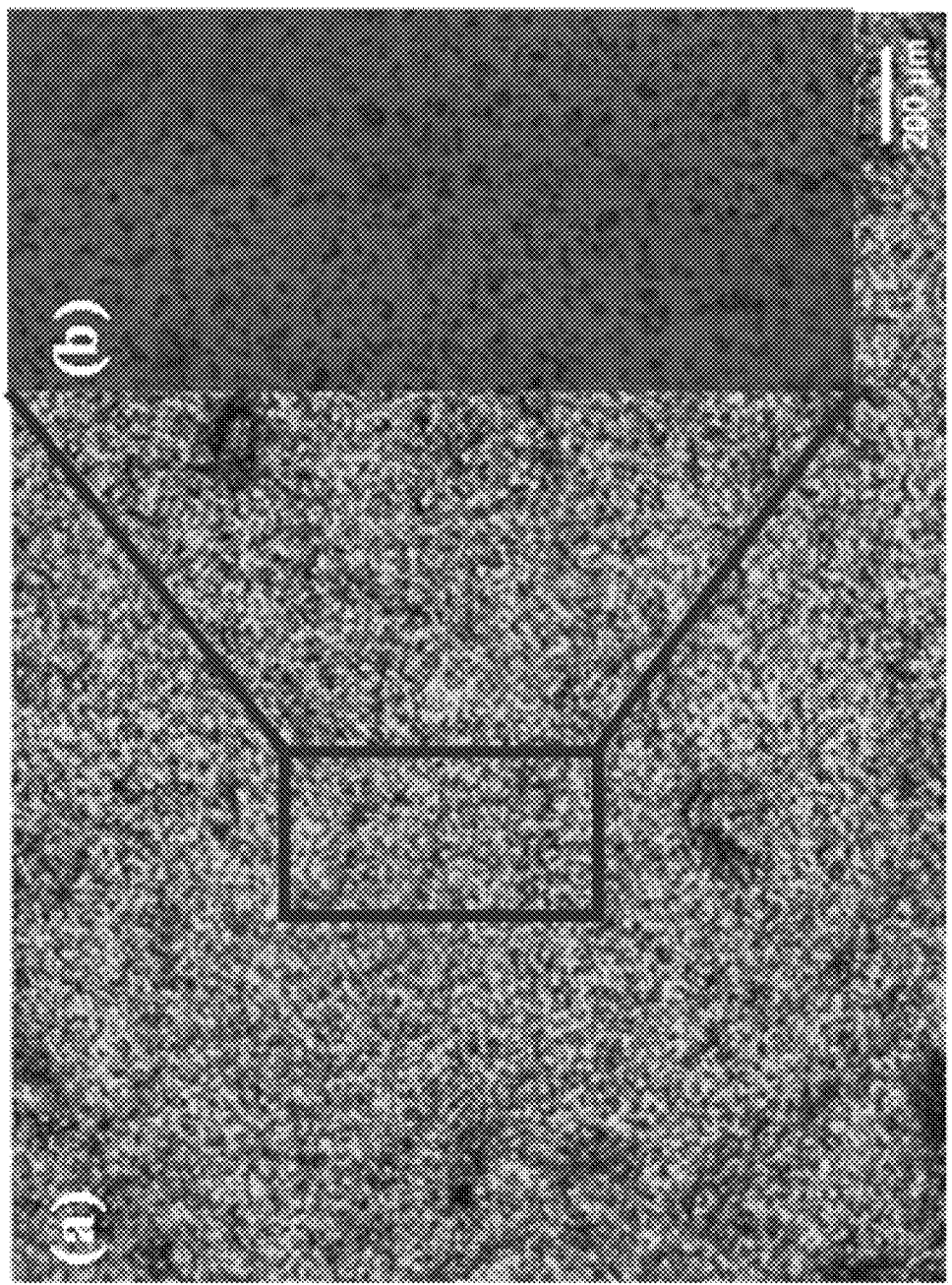
FIG. 14 is a representation of a micrograph of dispersed ferroparticles trapped inside the hydrogel network.

FIG. 14 is a representation of a micrograph of dispersed ferroparticles trapped inside the hydrogel network.

Figure 15:
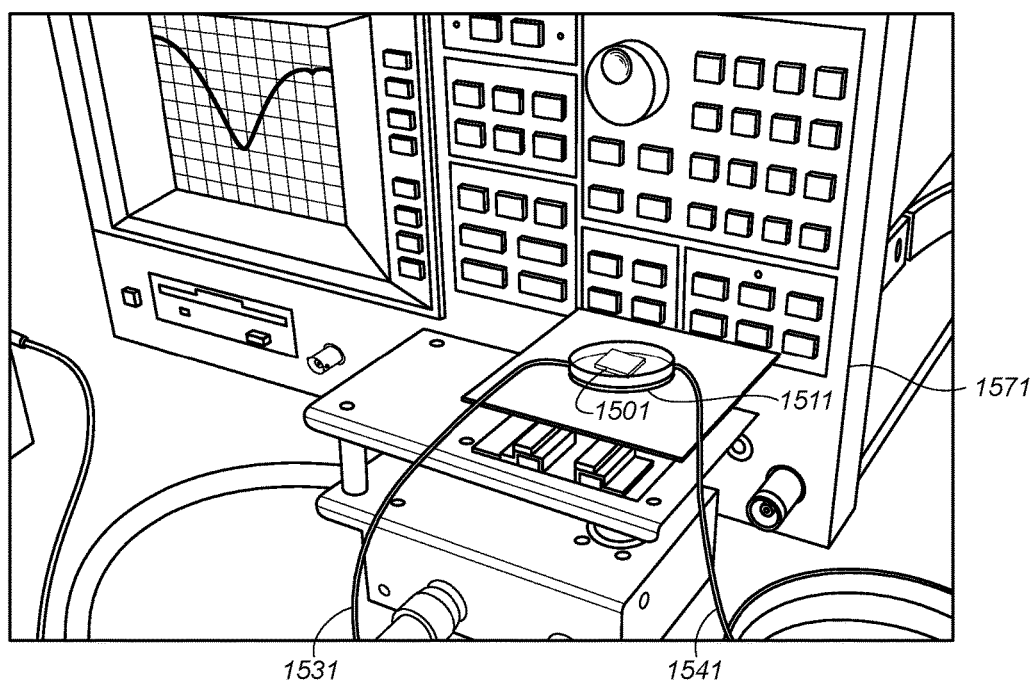
FIG. 15 shows a characterization setup for measuring properties of a ferrogel sensor.

FIG. 15 shows a characterization setup for measuring properties of sensor 1501. Readout coil 1511 is placed just below ferrogel sensor 1501. Experiments were conducted in a laser-machined acrylic chamber flow system. Three pH buffer solutions (pH4, pH5, and pH6) were prepared and successively injected into the chamber by a syringe pump at a constant flow rate of 0.3 ml/min through inlet 1531 and outlet 1541. The chamber was located over a readout coil connected to an impedance analyzer 1571 for resonance frequency readout (resolution: 16.23 kHz).

FIG. 16A shows a time series of measured resonant frequency. The abscissa is time in minutes and the ordinate is $f_{res}$ in MHz. In region 1606, the pH was 6; in region 1605, the pH was 5; and in region 1604, the pH was 4.

FIG. 16B shows the measured resonance frequency of the ferrogel sensor in response to step changes in pH (MHz vs. pH). As pH increases, the ferrogel swells, resulting in a lower resonance frequency. The measured parameters of the ferrogel sensor were overall dimension 1.5 cm×1.5 cm×463 μm; response time of the sensor 40 min; sensitivity 110 kHz/pH; and resolution 0.15 pH.

The invention is inclusive of combinations of the aspects described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A sensor for detecting a condition, the sensor comprising:
   a container;
   a hydrogel arranged within the container and configured to change thickness or volume in response to the condition;
   a plurality of magnetic particles arranged in the hydrogel so that a magnetic property of the hydrogel changes with changes of thickness or volume of the hydrogel; and
   a device coil arranged within the container and arranged with respect to the hydrogel so that changes in the magnetic property modulate an electrical property of the sensor, wherein terminals of the device coil are open.

2. The sensor according to claim 1, wherein the hydrogel is arranged in a layer and the device coil is a planar coil arranged substantially parallel to the layer.

3. The sensor according to claim 1, further including a substrate and a membrane arranged to form a cavity in which the hydrogel is located and can swell or shrink, wherein the membrane is configured to allow passage of a fluid across the membrane and block passage of particles of a predetermined size that are suspended in the fluid.

4. The sensor according to claim 3, wherein the hydrogel, the substrate, and the membrane are configured so that the hydrogel does not completely fill the cavity.

5. The sensor according to claim 3, further including an insulating layer arranged between the hydrogel and the device coil.

6. The sensor according to claim 3, wherein the device coil is arranged in the cavity and is electrically insulated, and the hydrogel is patterned.

7. The sensor according to claim 3, wherein the device coil is arranged at least partly in the hydrogel.

8. The sensor according to claim 1, wherein the electrical property of the sensor is resonant frequency or inductance.

9. The sensor according to claim 1, wherein the magnetic property of the hydrogel is magnetic permeability.

10. The sensor according to claim 1, further including a surface on which the hydrogel is patterned as an array of columns.

11. The sensor according to claim 10, wherein each column in the array of columns is cylindrical.

12. The sensor according to claim 1, wherein the hydrogel is formed about the device coil.

13. The sensor according to claim 1, further including a substrate on or in which the device coil is formed, wherein the substrate includes polystyrene (PS), polymethylmethacrylate (PMMA), or polyimide (PI).

14. The sensor according to claim 1, wherein the condition is moisture, temperature, or pH.

15. The sensor according to claim 1, wherein the condition is presence of glucose.

* * * * *